(12) United States Patent
Kitagawa

(10) Patent No.: US 12,031,158 B2
(45) Date of Patent: Jul. 9, 2024

(54) METHOD OF CULTURING CELLS, METHOD OF MANUFACTURING CELL SUPPORT COMPOSITE, CULTURED CELLS, AND CELL SUPPORT COMPOSITE

(71) Applicant: NIKKISO CO., LTD., Tokyo (JP)

(72) Inventor: Fumihiko Kitagawa, Kanazawa (JP)

(73) Assignee: NIKKISO CO., LTD., Tokyo (JP)

( * ) Notice: Subject to any disclaimer, the term of this patent is extended or adjusted under 35 U.S.C. 154(b) by 760 days.

(21) Appl. No.: 17/061,360

(22) Filed: Oct. 1, 2020

(65) Prior Publication Data

US 2021/0017498 A1 Jan. 21, 2021

Related U.S. Application Data

(63) Continuation of application No. PCT/JP2019/015351, filed on Apr. 8, 2019.

(30) Foreign Application Priority Data

Apr. 13, 2018 (JP) .................................. 2018-077560

(51) Int. Cl.
*C12N 5/071* (2010.01)

(52) U.S. Cl.
CPC ........ *C12N 5/0686* (2013.01); *C12N 2533/50* (2013.01); *C12N 2533/52* (2013.01)

(58) Field of Classification Search
CPC .............. C12N 5/0686; C12N 2533/50; C12N 2533/52

See application file for complete search history.

(56) References Cited

U.S. PATENT DOCUMENTS

| | | | |
|---|---|---|---|
| 5,686,289 | A | 11/1997 | Humes et al. |
| 6,060,270 | A | 5/2000 | Humes |
| 6,942,879 | B2 | 9/2005 | Humes |

FOREIGN PATENT DOCUMENTS

| | | | | |
|---|---|---|---|---|
| JP | 2011050358 | A | 3/2011 | |
| JP | 2017085963 | A * | 5/2017 | ............... C12N 5/00 |
| WO | WO-2007/023875 | A1 | 3/2007 | |
| WO | WO-2008/100226 | A1 | 8/2008 | |
| WO | WO-2017/082024 | A1 | 5/2017 | |
| WO | WO-2017/082026 | A1 | 5/2017 | |
| WO | WO-2017/082220 | A1 | 5/2017 | |
| WO | WO-2017082024 | A1 * | 5/2017 | ............. A61L 27/36 |
| WO | WO-2017082026 | A1 * | 5/2017 | ............. C07K 14/78 |

OTHER PUBLICATIONS

Gao, X., et al., "Basic structure and cell culture condition of a bioartificial renal tubule on chip towards a cell-based separation microdevice," Analytical Science 27(9): 907-912. doi: 10.2116/analsci.27.907. (Year: 2011).*
Narayanan K., et al., "Human embryonic stem cells differentiate into functional renal proximal tubular-like cells" Kidney International 83(4): 593-603. doi: 10.1038/ki.2012.442. (Year: 2013).*
Balzer, M. S., et al., "How Many Cell Types Are in the Kidney and What Do They Do?," Annual Review of Physiology 84: 507-531. doi: 10.1146/annurev-physiol-052521-121841. Epub Nov. 29, 2021. (Year: 2021).*
Masungi, C. et al., "Usefulness of a novel Caco-2 cell perfusion system II. Characterization of monolayer properties and peptidase activity," Pharmazie 64(1): 36-42. (Year: 2009).*
A Japanese Office Action with English translation issued in corresponding Japanese Patent Application No. 2020-513260, dated Jan. 25, 2022, 7 pages.
Zhang et al., "The impact of extracellular matrix coatings on the performance of human renal cells applied in bioartificial kidneys," Biomaterials, vol. 30, No. 15, May 1, 2009, pp. 2899-2911.
Jansen et al., "Biotechnological challenges of bioartificial kidney engineering," Biotechnology Advances, vol. 32, No. 7, Aug. 16, 2014, pp. 1317-1327.
Hoppensack et al., "A Human In Vitro Model That Mimics the Renal Proximal Tubule," Tissue Engineering, Part C, vol. 20, No. 7, Jul. 1, 2014, pp. 599-609.
Extended European Search Report dated Dec. 3, 2021 in EP Application No. 19784721.3, 8 pages.
International Search Report of PCT/JP2019/015351 and English translation, dated Jun. 25, 2019, 4 pages.
Written Opinion of the International Preliminary Examining Authority of PCT/JP2019/015351 and English translation, dated Apr. 14, 2020, 27 pages.
International Preliminary Report on Patentability of PCT/JP2019/015351 and English translation, dated Jul. 1, 2020, 25 pages.
Written Opinion of the International Searching Authority of PCT/JP2019/015351 and English translation, dated Jun. 18, 2019, 15 pages.
Slade et al., "Isolation of pepsin-resistant laminin fragments from human placenta: effect on epithelial cells cultured from the kidneys of patients with autosomal dominant polycystic kidney disease (ADPKD)", Biochemica et Biophysica Acta 1310 (1996) pp. 25-31, 7 pages.
Kariya et al., "Characterization of Laminin 5B and NH2-terminal Proteolytic Fragment of Its α3B Chain," The Journal of Biological Chemistry vol. 279, No. 23, Jun. 4, 2004, pp. 24774-24784, 11 pages.
Quaggin, Susan E. "Kindling the Kidney," N. Eng J. Med, Jan. 21, 2016, vol. 374(3), 5 pages.
Office Action dated Nov. 16, 2021 in JP Application No. 2020-513260, 13 pages, w/translation.
An Office Action in corresponding EP Application No. 19784721.3 dated Sep. 5, 2023 is attached, 4 pages.

* cited by examiner

*Primary Examiner* — Tracy Vivlemore
*Assistant Examiner* — Eric J Rogers
(74) *Attorney, Agent, or Firm* — Muncy, Geissler, Olds & Lowe, P.C.

(57) ABSTRACT

A method of culturing cells includes placing a cell suspension including i) one of more types of adhesion molecules selected from the group consisting of fragments of laminin molecules, fragments of a basement membrane matrix mixture, and a complete basement membrane matrix mixture and ii) kidney cells on a culture surface of a substrate; and culturing the kidney cells on the substrate to form a confluent monolayer of the cells.

8 Claims, 15 Drawing Sheets

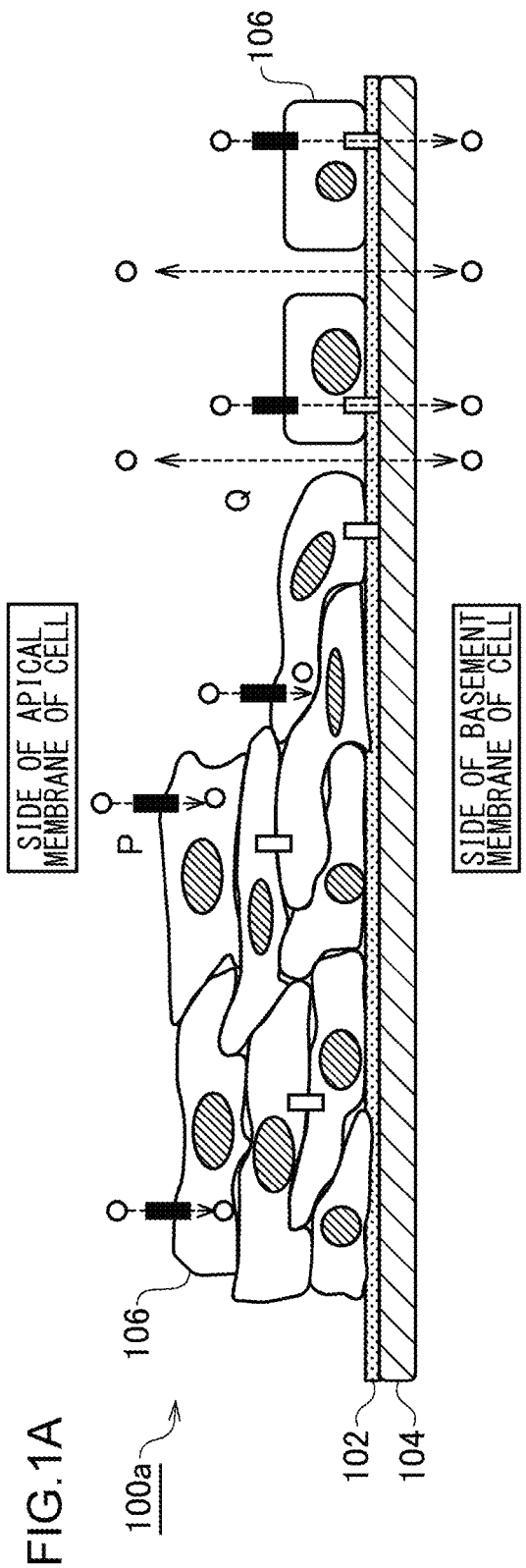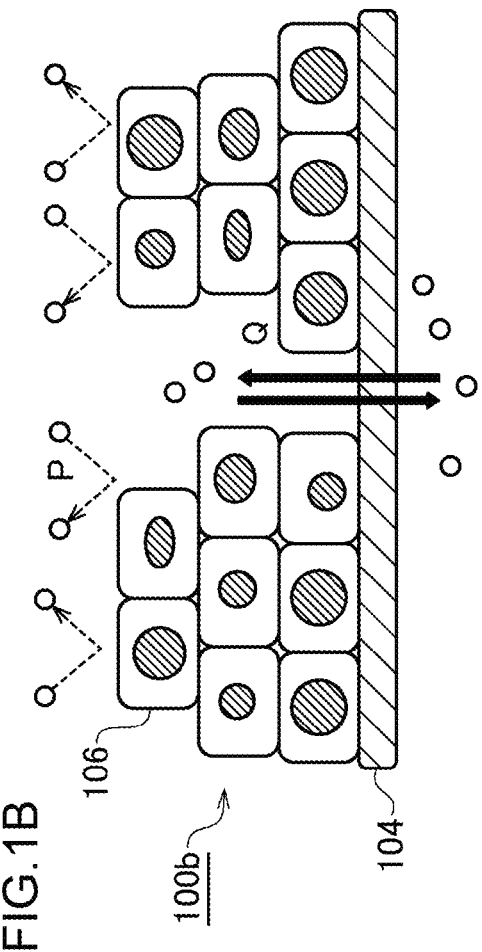

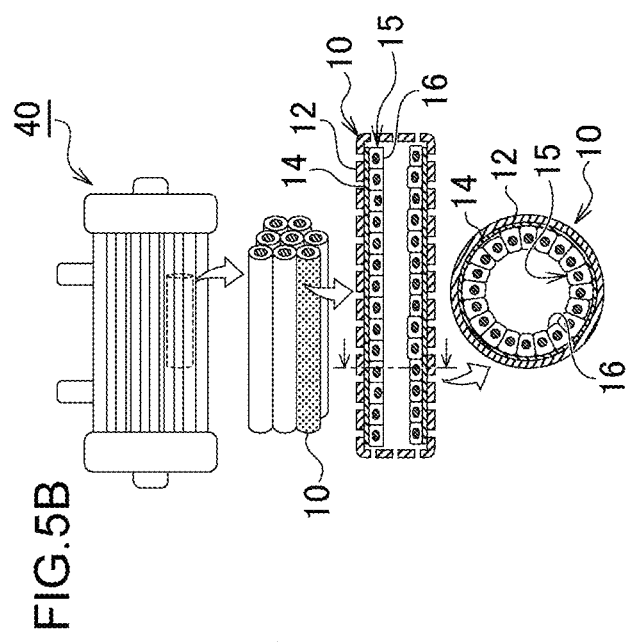
FIG.5A
FIG.5B
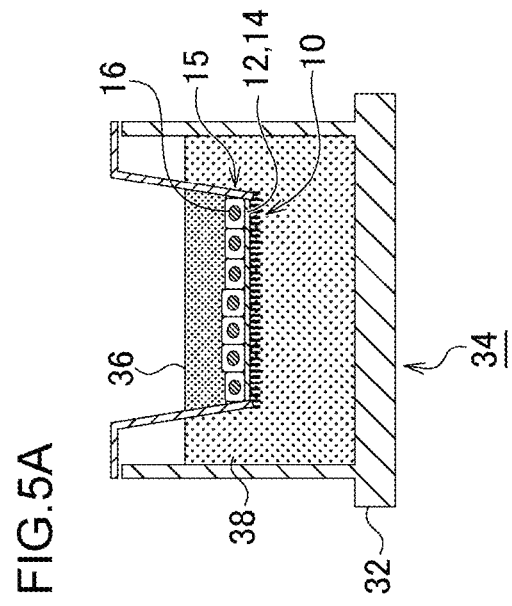
FIG.5C
FIG.5D
FIG.5E
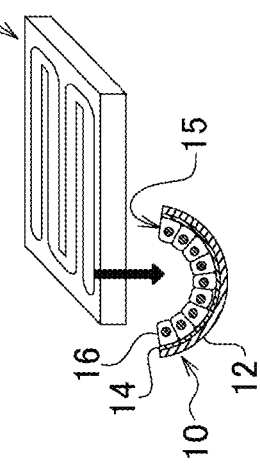
FIG.5F

FIG.6

| gene | Acronym | day4/day0 |
|---|---|---|
| aquaporin 1 | AQP1 | 0.412 |
| alanyl aminopeptidase | CD13 | 0.039 |
| sodium glucose cotransporter 2 | SGLT2 | 0.003 |
| $Na^+/K^+$ ATPase | Na/K ATPase | 0.138 |
| peptide transporter 1 | PEPT1 | 0.465 |
| multiple drug resistance 1 | MDR1 | 0.325 |
| organic anion transporter 1 | OAT1 | 0.208 |
| organic cation transporter novel 1 | OCTN2 | 0.031 |
| E-cadherin | E-cadherin | 0.005 |
| zonula occludens-1 | ZO-1 | 0.176 |

FIG.7

| Acronym | d4/d0 | d10/d0 | d16/d0 | d56/d0 |
|---|---|---|---|---|
| AQP1 | 0.01 | 0.61 | 7.24 | 2.32 |
| SGLT2 | 26.66 | 36.33 | 58.75 | 140.69 |
| Na/K ATPase | 3.00 | 3.16 | 15.64 | 4.38 |
| megalin | 9129.13 | 5954.95 | 18222.22 | 29735.74 |
| MDR1 | 1.57 | 1.33 | 3.07 | 1.56 |
| OAT1 | 597.61 | 1045.81 | 44154.09 | 14804.79 |
| OCT2 | 100.00 | 191.82 | 2180.35 | 137.86 |
| E-cadherin | 7.87 | 853.28 | 428.49 | 146.04 |

FIG.8

| Laminin511-E8 | | | | | | | | | | | |
|---|---|---|---|---|---|---|---|---|---|---|---|
| CONCENTRATION | AMOUNT OF CELL SUSPENSION SEEDED | L511 AMOUNT /cm² | NUMBER OF DAYS CULTURED | | | | | | | | |
| μg/ml | μl/1.9cm² | μg/cm² | 1 | 3 | 7 | 10 | 13 | 17 | 30 | 60 |
| 83 | 500.00 | 21.92 | ○ | ○ | ○ | ○ | ○ | ○ | ○ | ○ |
| 33 | 500.00 | 8.76 | ○ | ○ | ○ | ○ | ○ | ○ | ○ | ○ |
| 17 | 500.00 | 4.39 | ○ | ○ | ○ | ○ | ○ | ○ | ○ | △ |
| 7.5 | 500.00 | 1.97 | ○ | ○ | ○ | ○ | ○ | △ | △ | × |
| 2.5 | 500.00 | 0.66 | ○ | ○ | ○ | ○ | △ | × | × | × |
| 1.7 | 500.00 | 0.44 | ○ | ○ | ○ | △ | × | × | × | × |
| 0.8 | 500.00 | 0.22 | ○ | ○ | △ | × | × | × | × | × |
| 0.2 | 500.00 | 0.04 | ○ | ○ | △ | × | × | × | × | × |
| 0.0 | 500.00 | 0.00 | ○ | ○ | △ | × | × | × | × | × |

FIG.10

| | CONCENTRATION | AMOUNT OF CELL SUSPENSION SEEDED | L511 AMOUNT | NUMBER OF DAYS CULTURED | | | | | | | |
|---|---|---|---|---|---|---|---|---|---|---|---|
| | µg/ml | µl/1.9cm² | µg/cm² | 1 | 3 | 7 | 10 | 13 | 17 | 30 | 60 |
| Laminin511-E8 | 83 | 500.00 | 21.92 | ○ | ○ | ○ | ○ | ○ | ○ | ○ | ○ |
| | 33 | 500.00 | 8.76 | ○ | ○ | ○ | ○ | ○ | ○ | ○ | ○ |
| | 17 | 500.00 | 4.39 | ○ | ○ | ○ | ○ | ○ | ○ | ○ | ○ |
| | 7.5 | 500.00 | 1.97 | ○ | ○ | ○ | ○ | ○ | ○ | ○ | ○ |
| | 2.5 | 500.00 | 0.66 | ○ | ○ | ○ | ○ | ○ | ○ | △ | △ |
| | 1.7 | 500.00 | 0.44 | ○ | ○ | ○ | ○ | △ | ○ | △ | △ |
| | 0.8 | 500.00 | 0.22 | ○ | ○ | △ | △ | × | × | × | × |
| | 0.2 | 500.00 | 0.04 | ○ | ○ | ○ | × | × | × | × | × |
| | 0.0 | 500.00 | 0.00 | ○ | ○ | ○ | × | × | × | × | × |

FIG.12

| Laminin511 | | | | | | | | | | | |
|---|---|---|---|---|---|---|---|---|---|---|---|
| CONCENTRATION | AMOUNT OF CELL SUSPENSION SEEDED | L511 AMOUNT | NUMBER OF DAYS CULTURED | | | | | | | | |
| μg/ml | μl/1.9cm² | μg/cm² | 1 | 3 | 7 | 10 | 13 | 17 | 30 | 60 | |
| 83 | 500.00 | 21.92 | | | | | | | | | |
| 33 | 500.00 | 8.76 | ○ | ○ | △ | × | × | × | × | × | |
| 17 | 500.00 | 4.39 | | | | | | | | | |
| 7.5 | 500.00 | 1.97 | ○ | ○ | × | × | × | × | × | × | |
| 2.5 | 500.00 | 0.66 | ○ | ○ | × | × | × | × | × | × | |
| 1.7 | 500.00 | 0.44 | | | | | | | | | |
| 0.8 | 500.00 | 0.22 | ○ | ○ | × | × | × | × | × | × | |
| 0.2 | 500.00 | 0.04 | | | | | | | | | |
| 0.0 | 500.00 | 0.00 | ○ | ○ | × | × | × | × | × | × | |

FIG.14

FIRST MATRIGEL

| CONCENTRATION | AMOUNT OF CELL SUSPENSION SEEDED | FIRST MATRIGEL AMOUNT/cm² | NUMBER OF DAYS CULTURED | | | | | | |
|---|---|---|---|---|---|---|---|---|---|
| μg/ml | μl/1.9cm² | μg/cm² | 3 | 7 | 10 | 13 | 17 | 21 |
| 5000 | 500 | 1316 | × | × | × | × | × | × |
| 2500 | 500 | 658 | ○ | ○ | ○ | ○ | ○ | ○ |
| 1000 | 500 | 263 | ○ | ○ | ○ | ○ | ○ | ○ |
| 500 | 500 | 132 | ○ | ○ | ○ | ○ | ○ | ○ |
| 100 | 500 | 26 | ○ | ○ | ○ | ○ | ○ | ○ |
| 25 | 500 | 6.6 | ○ | ○ | ○ | | △ | △ |
| 5.0 | 500 | 1.3 | ○ | △ | × | × | × | × |

SECOND MATRIGEL (Growth Factor Reduced)

| CONCENTRATION | AMOUNT OF CELL SUSPENSION SEEDED | SECOND MATRIGEL AMOUNT/cm² | NUMBER OF DAYS CULTURED | | | | | | |
|---|---|---|---|---|---|---|---|---|---|
| μg/ml | μl/1.9cm² | μg/cm² | 3 | 7 | 10 | 13 | 17 | 21 |
| 4000 | 500 | 1053 | × | × | × | × | × | × |
| 2500 | 500 | 658 | ○ | ○ | ○ | △ | △ | △ |
| 1000 | 500 | 263 | ○ | ○ | ○ | ○ | ○ | ○ |
| 400 | 500 | 105 | ○ | ○ | ○ | ○ | ○ | ○ |
| 100 | 500 | 26 | ○ | ○ | ○ | ○ | ○ | ○ |
| 25 | 500 | 6.6 | ○ | ○ | ○ | △ | △ | △ |
| 5.0 | 500 | 1.3 | ○ | △ | × | × | × | × |

FIG.15
FIRST MATRIGEL
1316 μg/cm²     132 μg/cm²     1.3 μg/cm²
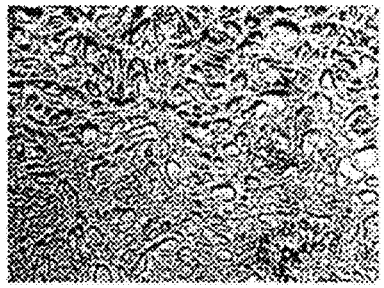 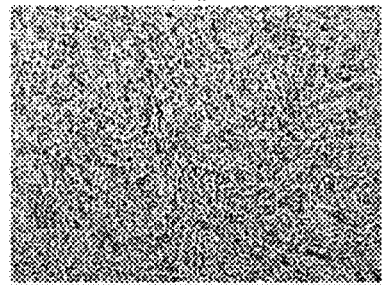 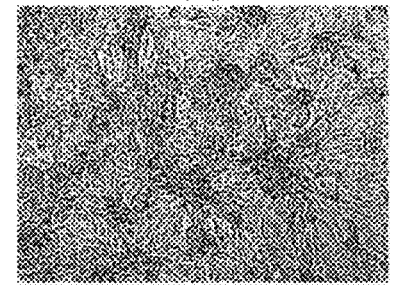
SECOND MATRIGEL (Growth Factor Reduced)
1053 μg/cm²     105 μg/cm²     1.3 μg/cm²
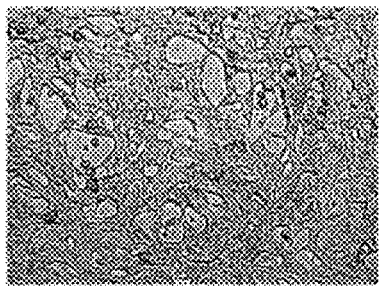 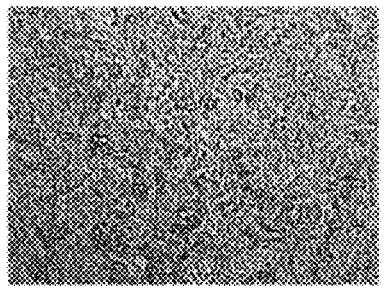 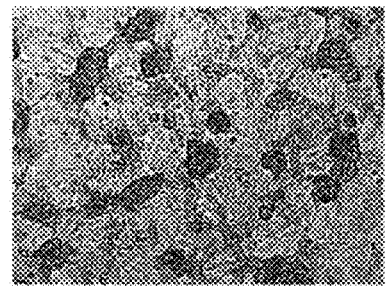

METHOD OF CULTURING CELLS, METHOD OF MANUFACTURING CELL SUPPORT COMPOSITE, CULTURED CELLS, AND CELL SUPPORT COMPOSITE

CROSS-REFERENCE TO RELATED APPLICATIONS

This application is based upon and claims the benefit of priority from the prior Japanese Patent Application No. 2018-077560, filed on Apr. 13, 2018, and International Patent Application No. PCT/JP2019/015351, filed on Apr. 8, 2019, the entire content of each of which is incorporated herein by reference.

BACKGROUND

Field of the Invention

The present invention relates to a method of culturing cells, a method of manufacturing a cell support composite, cultured cells, and a cell support composite.

Description of the Related Art

In recent years, development has proceeded to create a module as a bioartificial kidney which can substitute kidney functions of patients with kidney failure, having a polymer membrane such as a hollow fiber membrane, hybridized with kidney cells (cells having kidney functions) such as renal proximal tubule epithelial cell. In particular, considering manufacture, supply and use of such a hybrid module, there should be a need, in particular, for a bioartificial kidney capable of retaining the kidney functions over several weeks of longer.

Further, a drug administered to a living body demonstrates an action in vivo, and then excreted from the blood through the renal proximal tubule into the urine. Hence, the renal proximal tubule epithelial cell is susceptible to the drug, and may be damaged by the toxicity of the drug. It is therefore very beneficial in new drug development to develop a module for predicting the toxicity of a candidate substance against renal proximal tubule cells, and drug metabolism via renal proximal tubule cells. The aforementioned hybrid module, composed of the polymer membrane and renal proximal tubule epithelial cells, would be suitably applicable also as such a drug evaluation module.

In regard to the renal proximal tubule epithelial cells used for bio-artificial kidneys and drug evaluation modules, patent document 1 discloses a culturing technology of prolonging the division life span of renal proximal tubule epithelial cells so as to obtain a sufficient number of the cells, by suppressing the gene expression of the cell cycle control factors.

Patent Literature 1: JP2011-50358

The inventors of the present invention repeatedly conducted thorough investigations on the culturing technology for kidney cells, and the inventors found that in conventional culturing technologies, the physiological functions of kidney cells are deteriorated by culturing, and therefore, it is difficult to produce cultured cells that can be utilized for bio-artificial kidneys or drug evaluation modules. We have found that the physiological functions deteriorated due to culturing can be restored by culturing kidney cells in a confluent and monolayer state for a predetermined period of time. Meanwhile, it is desired to maintain the monolayer state of cells in a stable manner in order to restore the physiological functions in this method.

SUMMARY OF THE INVENTION

The present invention addresses the above-described issue, and an illustrative purpose thereof is to provide a technique for maintaining the monolayer state of cells in a stable manner.

One embodiment of the present invention relates to a method of culturing cells. The method of culturing cells includes: placing a cell suspension including i) one of more types of adhesion molecules selected from the group consisting of fragments of laminin molecules, fragments of a basement membrane matrix mixture, and a complete basement membrane matrix mixture and ii) kidney cells on a culture surface of a substrate; and culturing the kidney cells on the substrate to form a confluent monolayer of the cells. According to this embodiment, the monolayer state of the cells can be maintained in a stable manner.

Another embodiment of the present invention relates to a method of manufacturing a cell support composite. The method of manufacturing is a method of manufacturing a cell support composite including a substrate and a confluent monolayer of cultured cells stacked on a culture surface of the substrate and includes: forming the confluent monolayer on the substrate by the method of culturing cells according to any one of the above embodiments.

Still another embodiment of the present invention relates to cultured cells. The cultured cells are produced by the method of culturing cells according to any one of the above embodiments.

Still another embodiment of the present invention relates to a cell support composite. The cell support composite includes: a substrate; and a confluent monolayer of cultured cells according to the above embodiment stacked on a culture surface of the substrate.

Optional combinations of the aforementioned constituting elements, and implementations of the invention in the form of methods, apparatuses, and systems may also be practiced as additional modes of the present invention.

BRIEF DESCRIPTION OF THE DRAWINGS

Embodiments will now be described, by way of example only, with reference to the accompanying drawings which are meant to be exemplary, not limiting, and wherein like elements are numbered alike in several Figures, in which:

FIG. 1A and FIG. 1B schematically show a structure of a cell support composite according to a reference example;

FIG. 5A to FIG. 5F schematically show an exemplary application of the cell support composite according to the embodiment;

FIG. 6 is a chart summarizing time-dependent changes in gene expression levels in human renal proximal tubule epithelial cells adherently cultured;

FIG. 7 is a chart summarizing time-dependent changes in gene expression levels in human renal proximal tubule epithelial cells cultured in a state of cell monolayer;

FIG. 8 shows a relationship between the concentration of the adhesion molecules and the time-dependent change in the state of the cell monolayer;

FIG. 10 shows a relationship between the concentration of the adhesion molecules and the time-dependent change in the state of the cell monolayer in the case the coating agent layer is formed;

FIG. 12 shows a relationship between the concentration of the full-length laminin and the time-dependent change in the state of the cell monolayer;

FIG. 14 shows a relationship between the concentration of the first, second Matrigel and the time-dependent change in the state of the cell monolayer; and FIG. 15 is an optical micrographic image of cells on the 17th day of culture.

DETAILED DESCRIPTION OF THE INVENTION

Figure 2A:
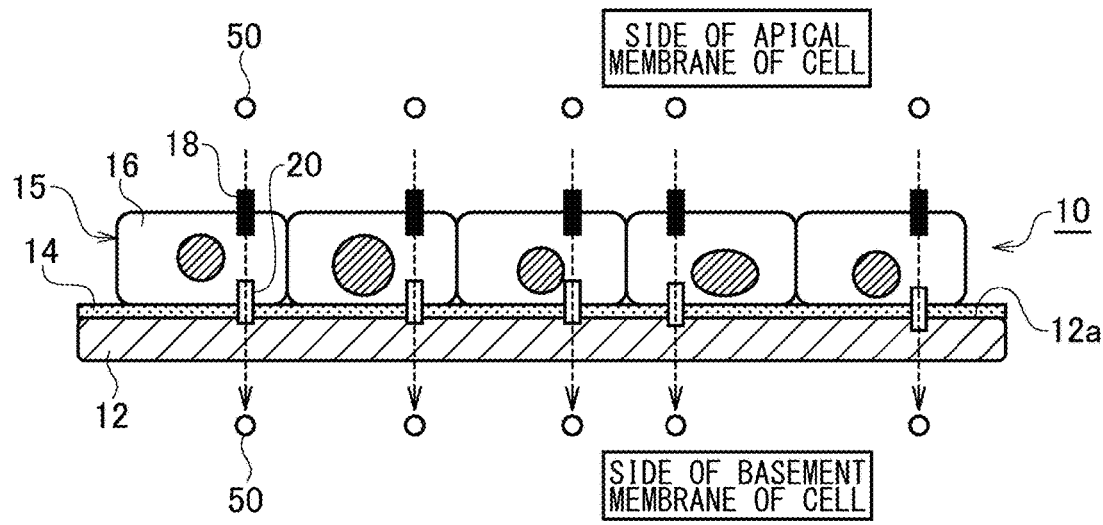
FIG. 2A to FIG. 2C schematically show cultured cells according to the embodiment and a structure of a cell support composite including the cultured cells.

One embodiment of the present invention relates to a method of culturing cells. The method of culturing cells includes: placing a cell suspension including i) one of more types of adhesion molecules selected from the group consisting of fragments of laminin molecules, fragments of a basement membrane matrix mixture, and a complete basement membrane matrix mixture and ii) kidney cells on a culture surface of a substrate; and culturing the kidney cells on the substrate to form a confluent monolayer of the cells. According to this embodiment, the monolayer state of the cells can be maintained in a stable manner.

In the above embodiment, a concentration of the fragments of laminin molecules in the cell suspension may be more than 0.66 μg per a unit area of the culture surface. Further, a concentration of the complete basement membrane matrix mixture in the cell suspension may be more than 1.3 μg and less than 1053 μg per a unit area of the culture surface. Further, the method may further include: coating the culture surface with a cellular adhesive substance, wherein the placing the cell suspension on the culture surface may include placing the cell suspension on the culture surface coated with the cellular adhesive substance.

Another embodiment of the present invention relates to a method of manufacturing a cell support composite. The method of manufacturing is a method of manufacturing a cell support composite including a substrate and a confluent monolayer of cultured cells stacked on a culture surface of the substrate and includes: forming the confluent monolayer on the substrate by the method of culturing cells according to any one of the above embodiments.

Still another embodiment of the present invention relates to cultured cells. The cultured cells are produced by the method of culturing cells according to any one of the above embodiments.

Still another embodiment of the present invention relates to a cell support composite. The cell support composite includes: a substrate; and a confluent monolayer of cultured cells according to the above embodiment stacked on a culture surface of the substrate.

The present inventors examined a technique of culturing kidney cells, and came to understand as below. Kidney cells such as renal proximal tubule epithelial cells, when isolated from the kidney by enzymatic treatment (primary cultured cells), will be dedifferentiated and gradually lose the function due to loss of an in vivo environment, and due to a culture environment such as two-dimensional culture on a petri dish. Hence, a simple culture of kidney cells will only result in proliferation of cells with poor physiological functions. A bioartificial kidney, when manufactured using dedifferentiated cells, would have only an insufficient level of reabsorption of useful ingredients in the blood plasma. In addition, a drug evaluation module, when manufactured using dedifferentiated cells, would not demonstrate highly accurate pharmacokinetics or toxic reaction.

In this background, the inventors have found a surprising fact that the physiological functions of dedifferentiated kidney cells can be restored by continuing to culture the cells in a confluent and monolayer state for a predetermined long period of time even if the functions has deteriorated temporarily. The inventors have also found that a specific culture can maintain the monolayer state of cells in a stable manner for the purpose of restoring the physiological functions by culturing the cells in the monolayer state.

Renal proximal tubule epithelial cells, when isolated from the kidney, cannot keep the original columnar cell structure, and deform into a flat shape. Moreover, the renal proximal tubule epithelial cells, when seeded on a petri dish or an artificial membrane, will lose the monolayer epithelial structure, creating gaps among the cells or multilayering of the cells. These events can make the bioartificial kidney less effective to reabsorb the useful ingredients. This can also degrade the accuracy of the drug evaluation module. In contrast, the present inventors found a technique for forming a stable monolayer epithelial structure on the substrate, using renal proximal tubule epithelial cells with their physiological functions restored. The embodiments were conceived on the basis of such contemplation.

A description will be given of suitable embodiments of the present invention with reference to the drawings. The preferred embodiments do not intend to limit the scope of the invention but exemplify the invention. Not all of the features and the combinations thereof described in the embodiments are necessarily essential to the invention. Like numerals are used to represent like elements, members, and processes and a description will be omitted as appropriate. The scales and shapes shown in the figures are defined for convenience's sake to make the explanation easy and shall not be interpreted limitatively unless otherwise specified. Terms like "first", "second", etc. used in the specification and claims do not indicate an order or importance by any means unless otherwise specified and are used to distinguish a certain feature from the others.

FIGS. 1(A) and 1(B) schematically show a structure of a cell support composite according to a reference example. FIG. 1(A) shows a cell support composite manufactured by an ordinary method of seeding cells on a substrate coated with a coating agent in advance. FIG. 1(B) shows a cell support composite manufactured by an ordinary method of seeding cells on a substrate not coated with a coating agent.

A cell support composite 100a shown in FIG. 1(A) is obtained by dropping a suspension of renal proximal tubule epithelial cells 106 that do not contain particular adhesion molecules on a substrate 104 such as an artificial membrane coated with a coating agent 102. In this cell support composite 100a, the renal proximal tubule epithelial cells 106 may be multilayered, or a gap may be created between cells.

A cell support composite 100b shown in FIG. 1(B) is obtained by dropping a suspension of the renal proximal tubule epithelial cells 106 that do not contain particular adhesion molecules on the substrate 104 not coated with the coating agent 102. In this cell support composite 100b, too, the renal proximal tubule epithelial cells 106 may be multilayered, or a gap may be created.

A region where the renal proximal tubule epithelial cells 106 are multilayered inhibits transfer of useful substances from side of the apical membrane of the cell toward the side of the basement membrane of the cell via a transporter (arrow P). Also, a concentration-dependent substance transfer via the substrate 104 could occur between neighboring renal proximal tubule epithelial cells 106 (arrow Q).

Figure 2B:
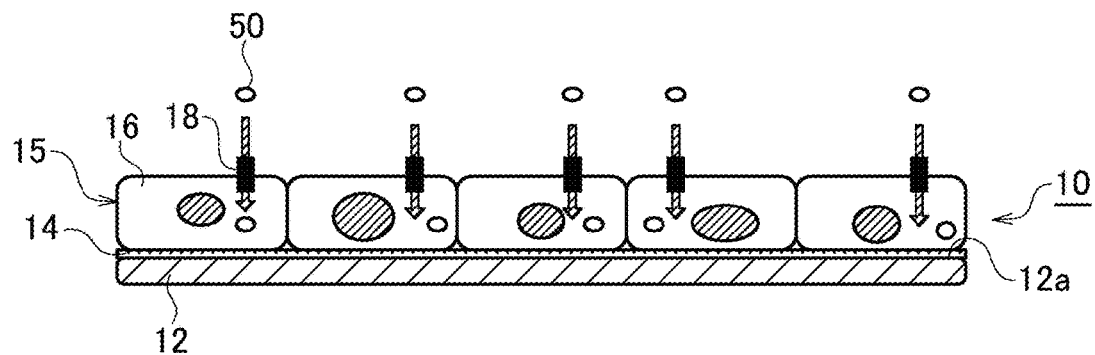
Figure 2C:
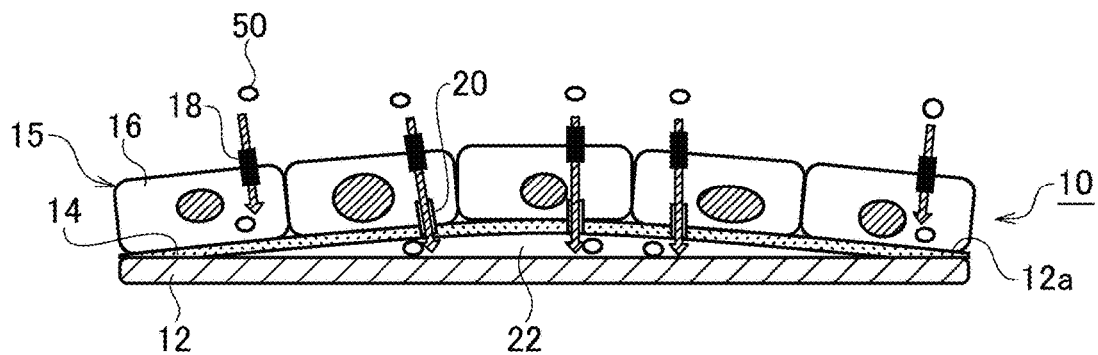

FIGS. 2(A) to 2(C) schematically show a cultured cell according to the embodiment and a structure of a cell support composite including the cultured cell. FIG. 2(A) shows a cell support composite in which a water-permeable substrate, i.e., a substrate having a relatively high water permeability is used. FIG. 2(B) shows a cell support composite in which a water-impermeable substrate, i.e., a substrate having a relatively low water permeability is used, viewed after a short lapse of time. FIG. 2(C) shows a cell support composite in which a water-impermeable substrate is used, viewed after a long lapse of time.

A cell support composite 10 includes a substrate 12, a coating agent layer 14, and a confluent monolayer 15 of cultured cells (hereinafter, referred to as a cell monolayer 15 as appropriate).

[Substrate]

The substrate 12 is composed of, for example, an artificial material. The substrate 12 has a culture surface 12a on which cells are seeded. The culture surface 12a means as least one flat or curved surface of the substrate 12. In the case the substrate 12 is a flat plate, the culture surface 12a means at least one of the principal surfaces of the flat plate. In the case the substrate 12 is cylindrical, the culture surface 12a means at least one of the inner side surfaces and the outer side surfaces of the cylinder.

As shown in FIG. 2(A), the substrate 12 has permeability to water and various ions. Furthermore, it is preferable that the substrate 12 has also permeability to sugars and low-molecular weight proteins. The cell support composite 10 having such substrate 12 is applicable, for example, to a bioartificial kidney. An useful substance 50 that resides on the side of the apical membrane of the cell passes through the cell support composite 10, by way of a transporter 18 on the side of the apical membrane of the cell and a transporter 20 on the side of the basement membrane of the cell provided in cultured cells 16 forming the cell monolayer 15 and via the substrate 12, and is transferred toward the side of the basement membrane of the cell.

In order to make the substrate have permeability to various substances, the substrate 12 is provided with, for example, pores. The average pore diameter of the pores provided in the substrate 12 is preferably 5 μm or smaller. When the average pore diameter is adjusted to 5 μm or less, the risk of the cultured cells 16 passing through the substrate 12 can be reduced. For example, Transwell (Corning Inc.; average pore diameter of 0.4 μm or 3.0 μm) can be used as the substrate 12.

Further, as shown in FIG. 2(B) and FIG. 2(C), the substrate 12 may not have permeability to water and various ions. The cell support composite 10 provided with the substrate 12 like this can be used as, for example, a drug evaluation module for evaluating drug metabolism (e.g., the amount of intake of drug by the cultured cells 16) and toxicity. A water-impermeable petri dish or well plate may be used for the substrate 12. The useful substance 50 that resides on the side of the apical membrane of the cell is incorporated, through the transporter 18 of the cultured cells 16, inside the cultured cells 16. For a short period of time since the start of use, only a small amount of the useful substance 50 moves through the transporter 20 of the cultured cells 16 toward the side of the basement membrane of the cell. Therefore, the cell monolayer 15 is not deformed as shown in FIG. 2(B). Meanwhile, after a long lapse of time, the amount of transfer of the useful substance 50 through the transporter 20 will increase, but the useful substance 50 cannot pass through the substrate 12, so that the cell monolayer 15 is elevated and forms a dome 22 as shown in FIG. 2(C).

Materials for composing the substrate 12 are exemplified by, but not specifically limited to, polystyrene, polycarbonate (PC), polyester (PET), polyester-based polymer alloy (PEPA), ethylene-vinyl alcohol copolymer (EVOH), polyethylene, a polysulfone (PSf), polyether sulfone (PES). The substrate 12 may have any shape exemplified by, but not specifically limited to, a culture well plate, a culture petri dish, an artificial membrane such as a hollow fiber membrane, Transwell and a flat sheet membrane, a micro-channel chip, solid particles, and hollow particles.

[Coating Agent Layer]

The coating agent layer 14 is a layer formed by a predetermined cellular adhesive substance. The cellular adhesive substance will be described in detail later. The coating agent layer 14 coats at least the culture surface 12a of the substrate 12. The coating agent layer 14 adheres to the culture surface 12a of the substrate 12 and is adhered to the substrate 12. By providing the coating agent layer 14, it is possible to reduce the amount of adhesion molecules described later added to the suspension of kidney cells, and, at the same time, to suppress multilayering of the cultured cells 16 or the creation of gaps more reliably. In other words, the cell monolayer 15 can be formed and maintained more reliably. The coating agent layer 14 can be omitted.

[Cell Monolayer]

The cell monolayer 15 is a confluent monolayer of cultured cells 16 stacked on the culture surface 12a of the substrate 12. The cultured cells 16 adhere to the culture surface 12a of the substrate 12 via the coating agent layer 14. In other words, the cultured cells 16 are adhered by the coating agent layer 14 to the substrate 12. In the case the coating agent layer 14 is omitted, the cultured cells 16 adhere to the substrate 12 directly. In any case, adhesion molecules (not shown) described layer also contribute to the fixing of the cultured cells 16 to the substrate 12. The cultured cells 16 have the transporter 18 located on the side of the apical membrane of the cell and the transporter 20 located on the side of the basement membrane of the cell.

The cultured cells 16 are produced by a method of culturing cells according to the embodiment. More specifically, the cultured cells 16 are produced by placing the cell suspension including particular adhesion molecules and kidney cells on the culture surface 12a of the substrate 12, culturing the kidney cells on the substrate 12, forming a confluent monolayer of the cultured cells 16, and culturing the cells in this state for a predetermined period of time.

For use in the cell support composite 10, the cultured cells 16 need to maintain the physiological functions of kidney cell. If kidney cells are cultured in an environment different from an in-vivo environment, cells will be dedifferentiated, and the physiological functions will be deteriorated. By culturing the cultured cells 16 in a confluent and monolayer state for a predetermined period of time as described above, on the other hand, the deteriorated physiological functions of kidney cells can be restored. The method of culturing cells will be described in detail later. Any improvement in the physiological functions deteriorated by culturing is encompassed by "restoration" according to this embodiment.

The kidney cells that serve as the base of the cultured cells 16 include histogenous kidney cells, or kidney cells derived from stem cells such as iPS cells, ES cells and Muse cells. The kidney cells include at least one of renal proximal tubule epithelial cells, distal kidney tubule epithelial cells, and collecting tubule epithelial cells. More specifically, the kidney cells are exemplified by human renal proximal tubule epithelial cells, human distal kidney tubule epithelial cells, and human collecting tubule epithelial cells collected and isolated from the kidney, and by renal proximal tubule epithelial cells, distal kidney tubule epithelial cells, and collecting tubule epithelial cells obtained by inducing differentiation from human iPS cells, human ES cells, or human Muse cells. More preferably, the kidney cells are renal proximal tubule epithelial cells. The kidney cells may also be exemplified by immortalized cells of the aforementioned kidney cells, established cells (HK-2 cells, etc.), genetically transformed cells obtained by introducing a gene into kidney cells to express a protein such as a specific transporter, and kidney precursor cells. Alternatively, instead of human-derived kidney cells, cells derived from other animal species (MDCK cells, LLC-PK1 cells, JTC-12 cells, etc.) may also be used as the kidney cells.

The aforementioned "monolayer" is a layer in which multilayering of the cultured cells 16 preferably does not occur at all. However, the "monolayer" may encompass a structure multilayered in part to the extent that decrease in the transfer efficiency of the substance due to multilayering does not pose a problem (substantial monolayer). Further, "confluent" means a state in which the area occupied by the cultured cells 16 in an observed image relative to the total area of the observed image is preferably 100%. For example, "confluent" means a state in which the proportion of the area occupied by the cells relative to the culture surface 12a as a whole is 100%, i.e., a state in which the cells have proliferated on the culture surface 12a without leaving any gap. However, the term "confluent" could also encompass a state in which gaps are created in part to the extent that a concentration-dependent substance transfer at gaps between adjacent cells does not pose a problem (substantially confluent state). Whether the structure is a monolayer and whether it is confluent can be easily determined by skilled persons.

(Method of Culturing cells and Method of Manufacturing Cell Support Composite)

FIGS. 3(A) to 3(D) show a first example of the method of culturing cells and the method of manufacturing a cell support composite according to the embodiment. The method of culturing cells according to the embodiment includes placing a cell suspension including particular adhesion molecules and the aforementioned kidney cells on the culture surface 12a of the substrate 12 and culturing the kidney cells on the substrate 12 and forming a confluent monolayer of the cells. According to the culturing method, the confluent monolayer of cells can be maintained in a stable manner. Therefore, the monolayer state of the cells can be maintained for a long period of time. By culturing the cells in this state for a predetermined period of time, the cultured cells 16 having the physiological functions can be produced.

The method of manufacturing a cell support composite according to the embodiment includes forming the cell monolayer 15 on the substrate 12 according to the method of culturing cells according to the embodiment. In other words, the substrate 12 used to culture kidney is used in the method of manufacturing a cell support composite according to the embodiment as the substrate 12 of the cell support composite 10. Therefore, the method of producing the cultured cells 16 can be directly interpreted as the method of manufacturing the cell support composite 10.

Figure 3A:
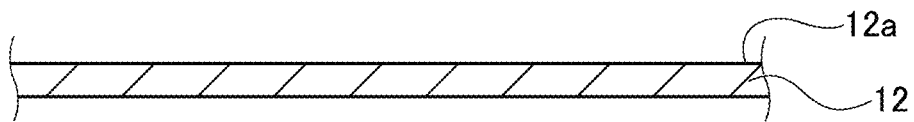
FIG. 3A to FIG. 3D show a first example of the method of culturing cells and the method of manufacturing a cell support composite according to the embodiment.

Specifically, the substrate 12 having the culture surface 12a is prepared as shown in FIG. 3(A). The culture surface 12a is not coated with a cellular adhesive substance. In other words, the coating agent layer 14 is not formed on the culture surface 12a. The substrate 12 forms a part of the cell support composite 10 that is ultimately obtained.

Figure 3B:
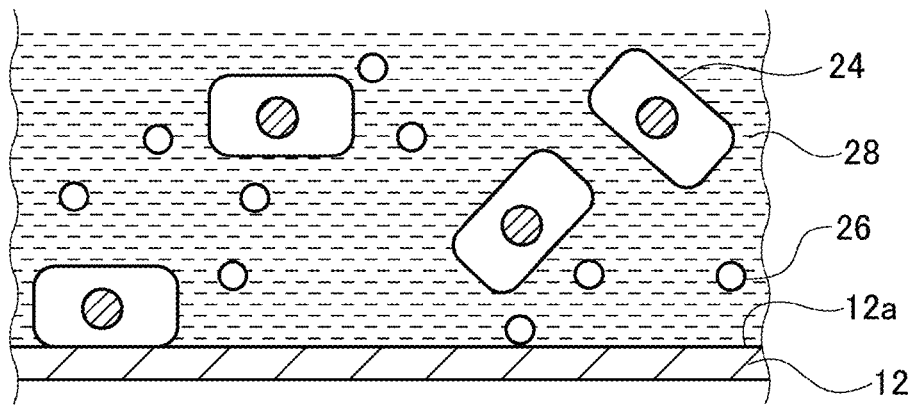

Subsequently, as shown in FIG. 3(B), a cell suspension 28 that contains the kidney cells 24 and adhesion molecules 26 is placed on the culture surface 12a of the substrate 12. For example, the cell suspension 28 is dropped onto the culture surface 12a. In this way, the kidney cells 24 are seeded on the culture surface 12a. The cell suspension 28 may be rested or shaken for a predetermined length of time before being placed on the culture surface 12a, in order to promote contact between the kidney cells 24 and the adhesion molecule 26. The length of time of rest or shaking is typically, but not specifically limited to, 30 minutes or shorter at room temperature or 37° C.

The cell suspension 28 includes a culture medium. A publicly known culture medium such as REGM (Lonza Inc.), EpiCM (ScienCell Research Laboratories, Inc.), Keratinocyte SFM (Life Technologies Corporation) can be used. A publicly known material necessary for culturing cells can be contained in the cell suspension 28 as appropriate.

The kidney cells 24 are available by a publicly known method. A commercial product of the kidney cells 24 can be used. The seeding density of the kidney cells 24 is preferably not less than 10,000 cells/cm$^2$ and not more than 300,000 cells/cm$^2$. The seeding density of 10,000 cells/cm$^2$ or higher makes it possible to form the cell monolayer 15 more reliably. It also inhibits the time elapsed until the cell monolayer 15 is formed from being significantly extended. The seeding density of 300,000 cells/cm$^2$ or lower can inhibit the kidney cells 24 from being aggregated without adhering to the culture surface 12a.

The adhesion molecules 26 contain one or more selected from the group consisting of fragments of laminin molecules, fragments of a basement membrane matrix mixture, and a complete basement membrane matrix mixture. Hereinafter, fragments of laminin molecules and fragments of a basement membrane matrix mixture may appropriately be referred to as a fragmented laminin and a fragmented basement membrane matrix mixture, respectively. Also, the complete laminin molecules and the complete basement membrane matrix mixture that originate the respective fragments may appropriately be referred to below as a full-length laminin and a full-length basement membrane matrix mixture.

(Fragments of Laminin Molecules)

The full-length laminin that originates a fragmented laminin has a heterotrimer structure having one α chain, one β chain and one γ chain, respectively. Currently, 5 types of α chains, 3 types of β chains and 3 types of γ chains have been identified. It is known that the laminin molecule forms at least 12 types of isoforms by combinations of these chains. The fragmented laminin in this embodiment is one or more types selected from laminin 111, laminin 211, laminin 221, laminin 311, laminin 332, laminin 421, laminin 511, and laminin 521.

The laminin molecule also encompasses variants (modified laminins) having a predetermined modification group at one or more sites of the aforementioned isoforms. The variant also encompasses a gene recombinant, i.e., a protein derived from introducing mutation in a protein obtained from a recombinant gene, a partial protein of a gene recombinant, and a protein having a peptide derived from a gene recombinant. The modifying group may be, for example, a growth factor binding molecule or a cell adhesion molecule.

Fragmented laminin is exemplified by a variant of E8 region containing the cell adhesion site (integrin-binding site) of Domain I in a full-length laminin (represented by laminin ***–E8). Examples of fragmented laminin like this include laminin 111-E8, laminin 211-E8, laminin 411-E8, laminin 421-E8, laminin 511-E8, and laminin 521-E8. The molecular weight of all of these is about one-fifth of the molecular weight of a full-length laminin. In the case laminin 511-E8 is used as the fragment of laminin molecule, commercially available laminin 511-E8 (iMatrix-511: Nippi Inc.) can be used, for example.

As the fragmented laminin, not only a modified body of the E8 region but also a laminin peptide having cell adhesion activity or a product obtained by synthesizing only cell active sites into a peptide can be used.

Examples of such a laminin peptide include a YIGSR-containing peptide derived from domain III of the β chain, a PDSGR-containing peptide derived from domain III of the β chain, an RYVVLPR-containing peptide derived from domain III of the β chain, an RGD-containing peptide derived from domain III of the α chain, a KAFDI-TYVRLKF-containing peptide derived from domain I of the γ chain, an IKVAV-containing peptide derived from domain I of the α chain, and an LRE-containing peptide derived from domain I of the β chain.

(Fragments or Complete Body of Basement Membrane Matrix Mixture)

The full-length basement membrane matrix mixture that originates the fragmented basement membrane matrix mixture is a mixture of extracellular matrix protein extracted from a murine sarcoma. The full-length basement membrane matrix mixture contains laminin, collagen IV and entactin as the principal constituents. The fragmented basement membrane matrix mixture containing at least one of laminin fragments, collagen IV fragments, and entactin fragments. The basement membrane matrix mixture is exemplified by Matrigel (registered trademark: Corning Inc.).

Matrigel is a soluble basement membrane matrix, extracted from an Engelbreth-Holm-Swarm (EHS) murine sarcoma that abundantly contains extracellular matrix proteins. In this embodiment, Matrigel not only includes normal Matrigel that contains a growth factor, but also Matrigel having the growth factor reduced therein as compared with the normal Matrigel (Growth Factor Reduced Matrigel Matrix). In the description below, normal Matrigel will be referred to as a first Matrigel, and growth factor-reduced Matrigel will be referred to as a second Matrigel. The first Matrigel and the second Matrigel are available, for example, from Corning Inc. The first Matrigel contains approximately 56% of laminin, approximately 31% of collagen IV, and approximately 8% of entactin. Meanwhile, the second Matrigel contains approximately 61% of laminin, approximately 30% of collagen IV, and approximately 7% of entactin.

As the basement membrane matrix mixture, also employable is a mixture that contains laminin, collagen IV, and entactin mixed according to a mass ratio of (ca. 56 to ca. 61):(ca. 30 to ca. 31):(ca. 7 to ca. 8).

The fragmented laminin and the fragmented basement membrane matrix mixture have molecular weights smaller than those of their complete bodies. The fragments can therefore enter finer regions. The adhesion molecules will become less likely to aggregate, making it possible to more uniformly disperse the adhesion molecules 26 in the cell suspension 28. This can maintain the cell monolayer 15 in a more stable manner than otherwise.

Each of the fragments of laminin molecules, the fragments of a basement membrane matrix mixture, and the complete basement membrane matrix mixture may be used alone, or two or more types may be mixed in use. A single type of isoform of fragmented laminin may be used alone, or a plurality of isoforms may be mixed in use. Similarly, a single type of the fragmented basement membrane matrix mixture and the full-length basement membrane matrix mixture may be employed alone, or a plurality of types may be mixed for use.

The concentration of the adhesion molecules 26 in the cell suspension 28 is preferably 0.04 μg or higher per unit area (1 cm$^2$) of the culture surface 12a, or 0.04 μg/cm$^2$ or higher, and, more preferably, higher than 0.22 μg/cm$^2$, and, still more preferably, higher than 0.66 μg/cm$^2$. With the concentration of the adhesion molecules 26 controlled to be 0.04 μg/cm$^2$ or higher, the adhesion molecules 26 will exhibit their function more reliably, and the structure of cell monolayer 15 will be maintained more reliably. Moreover, with the concentration of the adhesion molecules 26 controlled to be higher than 0.22 μg/cm$^2$, and, more preferably, higher than 0.66 μg/cm$^2$, the number of days over which the structure of the cell monolayer 15 is maintained can be extended.

With the concentration of the adhesion molecules 26 controlled to be higher than 0.66 μg/cm$^2$, in particular, the structure of the cell monolayer 15 is maintained more reliably over a period of practical use of the cell support composite 10. The period of practical use of the cell support composite 10 is preferably 16 days or longer since the formation of the cell monolayer 15. The concentration of the adhesion molecules 26 is more preferably 1.97 μg/cm$^2$ or higher. This can ensure more reliably that the period over which structure of the cell monolayer 15 is maintained is equal to or longer than the period of practical use of the cell support composite 10. The concentration of the adhesion molecules 26 is, for example, 22 μg/cm$^2$ or lower.

Figure 3C:
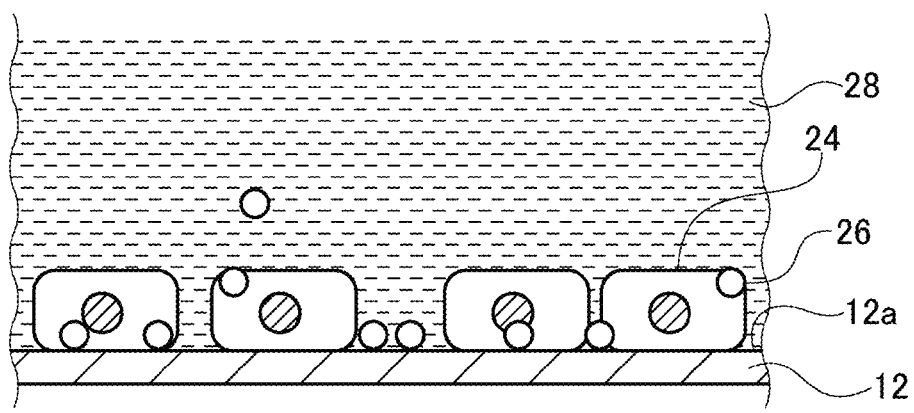

After dropping the cell suspension 28 onto the culture surface 12a, the kidney cells 24 seeded on the culture surface 12a are cultured as shown in FIG. 3(C). The cells are cultured under conditions of, for example, 37° C. and 5% $CO_2$. It is preferred to replace the culture medium periodically during the culture period. For example, the culture medium is replaced every day or every two days.

Figure 3D:
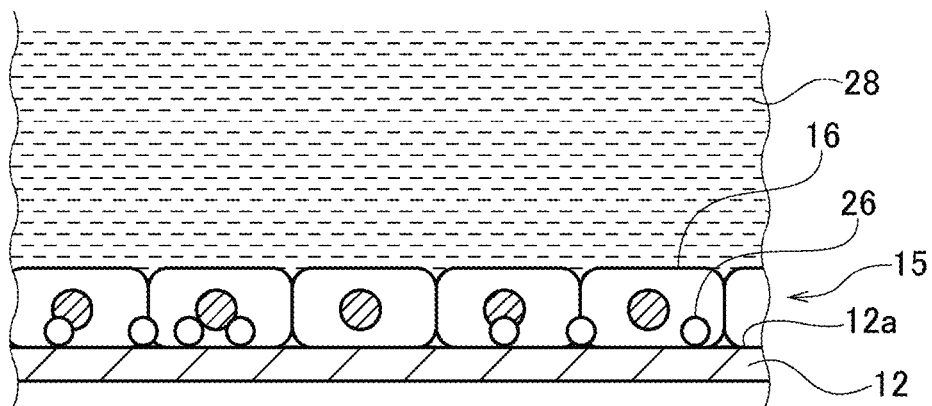

As a result, a confluent monolayer of the cultured cells 16, i.e., the cell monolayer 15, can be obtained as shown in FIG. 3(D). The adhesion molecules 26 are dispersed in the cell suspension 28. For this reason, adhesion between the kidney cells 24 to each other and adhesion between the kidney cells 24 and the culture surface 12a are enhanced by aid of the adhesion molecules 26. This can maintain the geometry of the cell monolayer 15, i.e., the monolayer state of the cultured cells 16 in a stable manner. The cell monolayer 15 is formed typically within a day (that is, within 24 hours) after seeding of the kidney cells 24 on the substrate 12.

Through the steps described above, the cell support composite 10 provided with the substrate 12 and the confluent monolayer of the cultured cells 16 stacked on the culture surface 12a of the substrate 12 can be obtained.

According to the first example described above, the cell support composite 10 not provided with the coating agent layer 14 shown in FIG. 2(A), etc. is obtained. Meanwhile, the cell support composite 10 provided with the coating agent layer 14 can be manufactured by the second example described below. FIGS. 4(A) to 4(D) show a second example of the method of culturing cells and the method of manufacturing a cell support composite according to the embodiment. In addition to the steps in the first example, the second example further includes coating the culture surface 12a with a cellular adhesive substance 30.

Figure 4A:
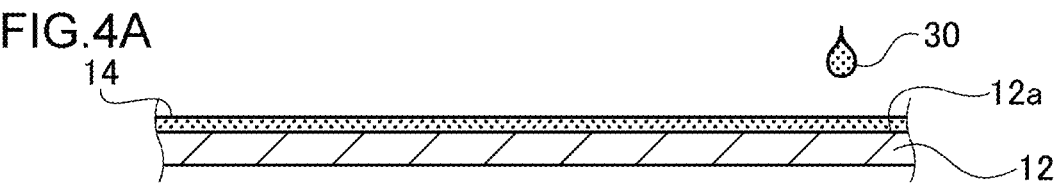
FIG. 4A to FIG. 4D show a second example of the method of culturing cells and the method of manufacturing a cell support composite according to the embodiment.

Specifically, as shown in FIG. 4(A), the culture surface 12a of the substrate 12 is coated with the cellular adhesive substance 30 to form the coating agent layer 14. The substrate 12 and the coating agent layer 14 form a part of the cell support composite 10 that is ultimately obtained. A publicly known cellular adhesive protein can be used as the cellular adhesive substance 30.

More specifically, the cellular adhesive substance 30 is exemplified by extracellular matrix protein such as collagen and gelatin; plasma component such as blood serum, blood albumin, and transferrin; and cell growth factor such as EGF (Epidermal Growth Factor), HGF (Hepatocyte Growth Factor), and BMP (Bone Morphogenetic Protein). The cellular adhesive substance 30 can be used alone, or two or more types can be mixed for use. The protein forming the cellular adhesive substance 30 is preferably derived from a human. Further, like the adhesion molecules 26, the cellular adhesive substance 30 may be fragments of laminin molecules, fragments of a basement membrane matrix mixture, and a complete basement membrane matrix mixture.

The cellular adhesive substance 30 is applied to the culture surface 12a in a mode of solution containing the cellular adhesive substance 30. It is preferred that the solution containing the cellular adhesive substance 30 be an aqueous solution that does not lower the activity of the cellular adhesive substance 30. Specifically, a neutral buffer and a cell culture medium are exemplified. A neutral buffer is exemplified by a phosphoric acid solution such as PBS (Phosphate buffered saline), a citric acid solution such as SSC (Standard Saline Citrate), a boric-acid solution such as TBE (Tris-borate-EDTA), a Tris buffer such as TE (Tris-EDTA Buffer), HEPES, etc. The cell culture medium is exemplified by DMEM, D-MEM/Ham'sF-12, MEM, α-MEM, IMDM, GMEM, REGM, EpiCM, Keratinocyte SFM, etc.

Generally, the cell culture medium contains a cell growth factor having the function of the cellular adhesive substance 30. By applying the medium on the culture surface 12a of the substrate 12, therefore, the coating agent layer 14 can be formed. The medium used to form the coating agent layer 14 is preferably the same as the medium contained in the cell suspension 28. In this case, after the coating agent layer 14 is formed, the subsequent dropping of the cell suspension 28 can be performed while maintaining the medium on the substrate.

The method of forming the coating agent layer 14, i.e., the method of conditioning the culture surface 12a is not limited to any particular method. For example, the solution of the cellular adhesive substance 30 is placed in contact with the culture surface 12a of the substrate 12, and the composite is rested or shaken at a predetermined temperature and for a predetermined period of time. The treatment temperature and the treatment time are exemplified by, but not limited to, 4° C. and 12 hours or longer, or 37° C. and two hours or longer. This forms the coating agent layer 14 on the culture surface 12a.

Figure 4B:
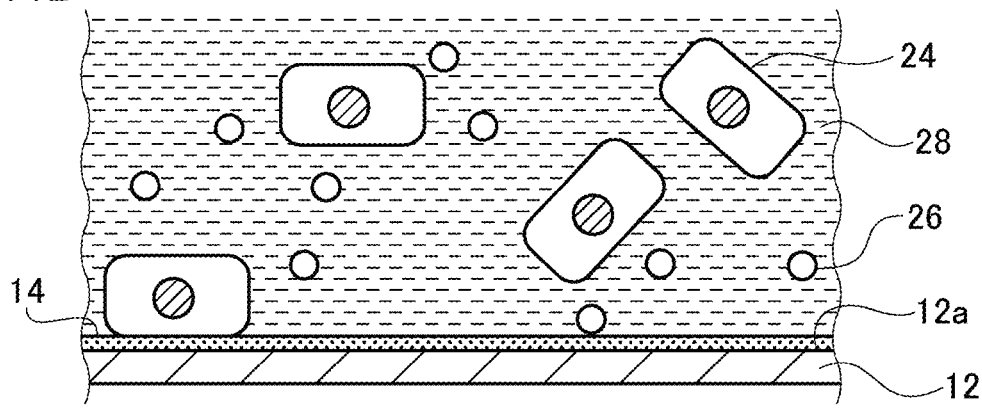

Subsequently, as shown in FIG. 4(B), the cell suspension 28 including the kidney cells 24 and the adhesion molecules 26 is placed on the culture surface 12a of the substrate 12. Since the coating agent layer 14 is formed on the culture surface 12a, the kidney cells 24 are seeded on the coating agent layer 14. The types of the kidney cells 24 and the adhesion molecules 26, the seeding density of the kidney cells 24, the concentration of the adhesion molecules 26, etc. are the same as those of the first example.

Figure 4C:
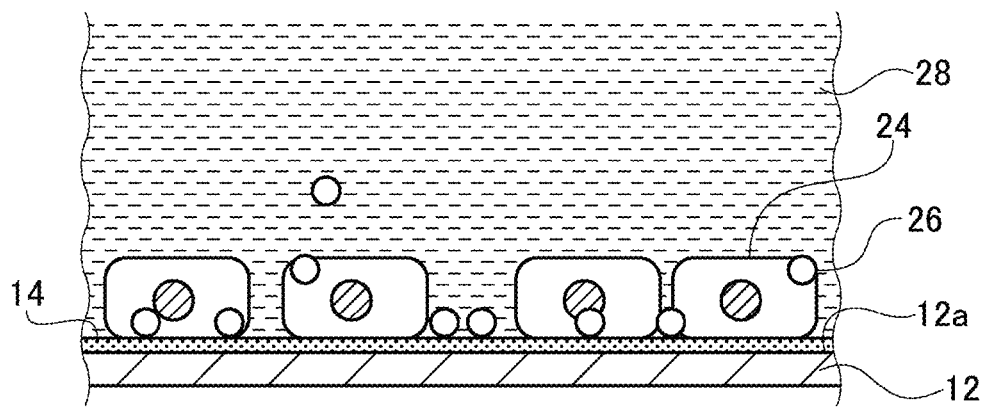

As shown in FIG. 4(C), the kidney cells 24 seeded on the culture surface 12a are cultured. The culturing condition is the same as that of the first example.

Figure 4D:
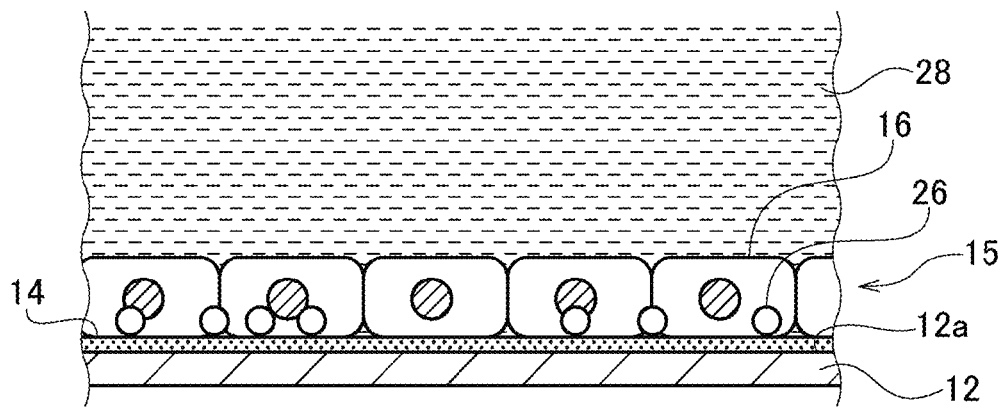

As a result, the cell monolayer 15 is obtained as shown in FIG. 4(D). The adhesion molecules 26 are dispersed in the cell suspension 28. Therefore, adhesion between the kidney cells 24 to each other and adhesion between the kidney cells 24 and the coating agent layer 14 are enhanced by aid of the adhesion molecules 26. This can maintain the monolayer state of the cultured cells 16 in a stable manner.

Further, adhesion of the kidney cells 24 to the substrate 12 is enhanced also by the coating agent layer 14. This makes it possible to maintain the monolayer state of the cultured cells 16 in a stable manner, while also reducing the amount of the adhesion molecules 26 used. The cell monolayer 15 is formed typically within a day (that is, within 24 hours) after seeding of the kidney cells 24 on the substrate 12. Through the steps described above, the cell support composite 10 structured such that the substrate 12, the coating agent layer 14, and the cell monolayer 15 are stacked in the stated order can be obtained.

Preferably, the method of culturing cells and the method of manufacturing a cell support composite include culturing cells for not shorter than 16 days and not longer than 60 days in a state in which the cell monolayer 15 is formed. In this way, the physiological functions of the kidney cells 24 dedifferentiated due to disappearance of an in-vivo environment can be restored. In other words, the cultured cells 16 in a state in which physiological functions are expressed at a higher level than immediately after the cell monolayer 15 is formed can be obtained.

The culture period of 16 days or longer ensures that the cultured cells 16 having restored physiological functions can be obtained more reliably. It also makes it possible to restore the physical functions more extensively. Further, the culture period of 60 days or shorter makes it possible to maintain the structure of the cell monolayer 15, i.e., the confluent and not-multilayered state of the cultured cells 16 more reliably. The kidney cells 24 for which the physiological functions are restored in a separate treatment may be seeded on the culture surface 12a. In this case, the cell support composite 10 can be put to use without waiting for an end of the culture period of 16 days or longer (for example, one day after the culturing).

The concentration of the cultured cells 16 in the cell monolayer 15 is preferably not less than 25,000 cells/cm$^2$ and not more than 75,000 cells/cm$^2$. The cell concentration of 25,000 cells/cm$^2$ or more makes it possible to form the cell monolayer 15 more reliably. It also makes it possible to obtain a sufficient adhesion state between cells in the cell monolayer 15. Consequently, the cultured cells 16 having restored the physiological functions can be formed more reliably. The cell concentration of 75,000 cells/cm$^2$ or less can inhibit formation of an aggregate of the cultured cells

16. By inhibiting formation of an aggregate, gaps are inhibited from being created around the aggregate. Accordingly, the structure of the cell monolayer 15 can be maintained more reliably.

Further, by maintaining the structure of the cell monolayer 15, the stack of the substrate 12 and the cell monolayer 15, and the stack of the substrate 12, the coating agent layer 14, and the cell monolayer 15 can be directly used as the cell support composite 10.

[Apparatus Using Cell Support Composite]

FIG. 5(A) to FIG. 5(F) schematically show an exemplary application of the cell support composite according to the embodiment. FIG. 5(A) to FIG. 5(F) show a part of a structure having incorporated therein the cell support composite. The cell support composite 10 of this embodiment is applicable to various apparatuses.

For example, FIG. 5(A) shows a first apparatus 34 equipped with Transwell 32, having the cell support composite 10 incorporated therein. Transwell 32, having a known structure, will not be detailed here. In the first apparatus 34, a first liquid 36 that contains a predetermined substance is fed on the side where the cell monolayer 15 is arranged. The predetermined substance in the first liquid 36 is incorporated into the cultured cells 16, passes through the cell support composite 10, and moves to a second liquid 38 placed on the opposite side of the first liquid 36, sandwiching the cell support composite 10 in between. The first apparatus 34 can be used as, for example, a drug evaluation module for investigating a function of a cell or the uptake and excretion of a drug with a very small amount of liquid.

FIG. 5(B) shows a second apparatus 40 having incorporated therein the cell support composite 10, in which a hollow fiber membrane is used as the substrate 12. In the second apparatus 40, the coating agent layer 14 and the cell monolayer 15 are formed in a tubular cavity of the hollow fiber membrane used as the substrate 12. Upon feeding of a liquid through the tubular cavity of the hollow fiber membrane, the second apparatus 40 can make the cultured cells 16 incorporate the predetermined substance in the liquid and then move the substance outside of the tubular cavity of the hollow fiber membrane. The second apparatus 40 is applicable, for example, as a bioartificial kidney module that collects a useful substance from plasma components obtained after filtration through a blood filter.

FIG. 5(C) shows a microchannel chip 42 having incorporated therein the cell support composite 10. In the microchannel chip 42, the substrate 12 composes a microchannel. The coating agent layer 14 and the cell monolayer 15 are formed on the inner wall of the microchannel. In the microchannel chip 42, a microvolume of liquid is allowed to flow in the channel, that is, on the side the cultured cells 16 are arranged. The predetermined substance in the liquid is then incorporated into the cultured cells 16. The microchannel chip 42 can be used as, for example, a drug evaluation module for investigating a function of a cell or uptake and excretion of a drug only with a very small amount of liquid.

FIG. 5(D) shows the cell support composite 10 composing a hollow microcarrier 44. FIG. 5(E) shows the cell support composite 10 composing a solid microcarrier 46. In the hollow microcarrier 44 and the solid microcarrier 46, the substrate 12 composes the carrier body. The coating agent layer 14 and the cell monolayer 15 are formed on the outer face of the substrate 12. To the hollow microcarrier 44 and the solid microcarrier 46, a microvolume of liquid is fed on the side the cultured cells 16 are arranged. The predetermined substance in the liquid is then incorporated into the cultured cells 16. The hollow microcarrier 44 and the solid microcarrier 46 can be used as, for example, a drug evaluation module for investigating a function of a cell or uptake and excretion of a drug only with a very small amount of liquid.

FIG. 5(F) shows a well plate 48 having incorporated therein the cell support composite 10. In the well plate 48, the cell support composite 10 is arranged on the bottom face of the well. In this arrangement, the cell monolayer 15 faces upward in the well. In the well plate 48, a microvolume of liquid 49 is dispensed in the well. The predetermined substance in the liquid 49 is then incorporated into the cultured cells 16. The well plate 48 can be used as, for example, a drug evaluation module for investigating a function of a cell or uptake and excretion of a drug only with a very small amount of liquid. In place of the well plate 48, a culture dish (petri dish, etc.) may have incorporated therein the cell support composite 10.

The aforementioned module having incorporated therein the cell support composite 10 is used, while being properly enclosed in a cartridge just like the second apparatus 40.

As has been described above, the method of culturing cells of this embodiment includes placing the cell suspension 28 including i) one or more types of adhesion molecules 26 selected from the group consisting of fragments of laminin molecules, fragments of a basement membrane matrix mixture, and a complete basement membrane matrix mixture ii) and the kidney cells 24 on the culture surface 12*a* of the substrate 12; and culturing the kidney cells 24 on the substrate 12 to form a confluent monolayer of the cells. Thus, the monolayer state of the cells can be maintained in a stable manner by a simple process of adding the adhesion molecules 26 to the cell suspension 28. In this way, the physiological functions of the kidney cells 24 deteriorated by culturing can be restored more reliably.

In the method of culturing according to the embodiment, the physiological functions are re-obtained, i.e., the cells are redifferentiated, by culturing the kidney cells 24 that have been dedifferentiated and lost the physiological functions in a confluent and monolayer state. Thus, according to the culturing method of the embodiment, the cultured cells 16 for which the physiological functions are in a more proper state than in the related art can be obtained.

To maintain the cell monolayer 15 in a stable manner, it is conceivable to apply a solution of the adhesion molecules 26 to the culture surface 12*a* in advance and culture the kidney cells 24 accordingly, i.e., to seed the kidney cells 24 on the coating agent layer 14 comprised of the adhesion molecule 26. However, this method produces imbalance in the solution of the adhesion molecules 26 in the process of drying the solution, which could lead to uneven coating of the adhesion molecules 26. Uneven coating of the adhesion molecules 26 results in formation of a portion that adheres to the kidney cells 24 easily and a portion that does not adhere to the kidney cells 24 easily on the culture surface 12*a*. This could result in a certain region of the coating agent layer 14 providing a basis for aggregation of the kidney cells 24, making it difficult to maintain the cell monolayer 15 in a stable manner.

It is conceivable to increase the amount of the adhesion molecule solution added to the culture surface 12*a* to prevent localization of the adhesion molecules 26, but then this leads to an increase in the cost of manufacturing the cultured cells 16 and the cell support composite 10. Further, the substrate 12 having a relatively complicated shape is used in a bioartificial kidney or a pharmacokinetics evaluation module. In that case, the adhesion molecules 26 could also be applied to the surface of the substrate 12 other than the culture surface 12a. As a result, the amount of the adhesion molecules 26 used is increased, and the cost will be increased. By way of contrast, the mode of adding the adhesion molecules 26 to the cell suspension 28 makes it possible to disperse the adhesion molecules 26 on the culture surface 12a and around the kidney cells 24 evenly, while also inhibiting an increase in the amount of the adhesion molecules 26 used. Accordingly, the structure of the cell monolayer 15 can be maintained in a stable manner, while also inhibiting an increase in the cost.

Further, the method of manufacturing the cell support composite 10 according to the embodiment includes forming the cell monolayer 15 on the substrate 12 according to the method of culturing cells according to the embodiment. Thus, by manufacturing the cell support composite 10 using highly functional cells obtained by the method of culturing cells according to the embodiment, it is possible to provide high performance bioartificial organs or in vitro evaluation systems. Further, since the stability of the cell monolayer 15 is improved, microscopic observation of confluence of the cultured cells 16 on the substrate 12 can be omitted. Accordingly, the cell support composite 10 having a desired shape can be manufactured easily. It is also possible to manufacture a large amount of cell support composites 10 with the same structure.

An example of the embodiment further includes applying the cellular adhesive substance 30 on the culture surface 12a. The cell suspension 28 is placed on the culture surface 12a coated with the cellular adhesive substance 30. Thus, by conditioning the culture surface 12a before placing the cell suspension 28, the structure of the cell monolayer 15 can be maintained stable for a longer period of time. It can also reduce the amount of the adhesion molecules 26 necessary to maintain the stable structure of the cell monolayer 15.

The present invention is not limited to the embodiment described above, and modifications such as design changes may be made based on the knowledge of a skilled person. Embodiments resulting from such modification are also encompassed by the scope of the present invention. A new embodiment created by a combination of the embodiment described above with the following variations will provide the combined advantages of the embodiment and the variation as combined.

Examples

[Analysis of Gene Expression in Renal Proximal Tubule Epithelial Cells: Test 1]

Deterioration of physiological functions in renal proximal tubule epithelial cells was checked by Test 1. First, 100,000 human renal proximal tubule epithelial cells (Lonza Inc.) were seeded onto a 60-mm Petri dish (Corning Inc.) coated with a gelatin solution (Sigma-Aldrich Corp.). Then, the cells were cultured using REGM (Lonza, Inc.) as a medium under the conditions of 37° C. and 5% $CO_2$.

mRNAs were extracted from the renal proximal tubule epithelial cells immediately after seeding (that is, zero hours) and on day 4 of culture (that is, 96 hours) using an RNeasy Mini Kit (QIAGEN NV), and the mRNAs were purified. Subsequently, cDNAs were synthesized from the purified mRNAs using a QuantiTect Reverse Transcription Kit (QIAGEN NV). These cDNAs were used as templates and the amounts of expression of the respective genes of AQP1, CD13, SGLT2, Na/K ATPase, PEPT1, MDR1, OAT1, OCTN2, E-cadherin, and ZO-1 were measured by a real time PCR method using Thermal Cycler Dice Real Time System I (Takara Bio Inc.).

These genes are genes related to the physiological functions of kidney cells. Specifically, AQP1 (aquaporin 1) is a gene encoding a protein involved in the transportation of water. CD13 (alanyl aminopeptidase) is a gene encoding a protein involved in peptidization of protein. SGLT2 (sodium glucose cotransporter 2) is a gene encoding a protein involved in sodium and glucose transport. Na/K ATPase is a gene encoding a protein involved in ion transport. PEPT1 (peptide transporter 1) is a gene encoding a protein involved in peptide transport. MDR1 (multiple drug resistance 1), OAT1 (organic anion transporter 1) and OCTN2 (organic cation transporter novel 1) are genes encoding proteins involved in drug transport. E-cadherin and ZO-1 (zonula occludens-1) are genes encoding proteins involved in intercellular junction.

Ratio of the expression level on the 4th day of culture relative to the expression level immediately after seeding (day 4/day 0) was calculated for each gene. Results are summarized in FIG. 6. FIG. 6 is a chart summarizing time-dependent changes in gene expression levels in human renal proximal tubule epithelial cells adherently cultured. As summarized in FIG. 6, the ratio was found to be smaller than 1, for all genes. That is, the expression levels of the individual genes on the 4th day of culture were found to decline from the levels immediately after start of culture. The results taught that the renal proximal tubule epithelial cells showed declined gene expression levels by two-dimensional culture in the petri dish, that is, they are dedifferentiated. Even immediately after seeding, the renal proximal tubule epithelial cells are supposed to have the physiological functions declined to a certain degree.

[Analysis of Time-dependent change in Gene Expression Levels: Test 2]

Test 2 was carried out to confirm restoration of physiological functions of the renal proximal tubule epithelial cells cultured for a long period of time by referring to the variation in the gene expression levels. First, a suspension of human renal proximal tubule epithelial cells (Lonza Inc.) that are dedifferentiated as in Test 1 was prepared. Further, the culture surface of the 12-well Transwell (Corning Inc.) is coated with a laminin 511-E8 solution (Nippi Inc.) conditioned to 20 μg/ml. The conditioned cell suspension is dropped onto the Transwell thus coated. The number of seeded cells is controlled to be 200,000 (the seeding density is 179,000 cells/$cm^2$). The cells were cultured using REGM (from Lonza Inc.) as a medium under conditions of 37° C. and 5% $CO_2$ to form a cell monolayer. The cells were cultured for 56 days since the day of formation of the cell monolayer. The medium was exchanged every two days.

An optical microscopic observation of the cells confirmed that confluence is reached substantially within one day. Therefore, the culture period since the seeding can be equated with the culture period since the day of formation of the cell monolayer. mRNA was extracted from the renal proximal tubule epithelial cells immediately after the formation of the cell monolayer (that is, after 0 hours) and from the renal proximal tubule epithelial cells on days 4, 10, 16, 56 (that is after 96, 240, 384, 1344 hours) since the day of formation of the cell monolayer, using RNeasy Mini Kit (QIAGEN), and was purified. Next, cDNA was synthesized from the purified mRNA, using QuantiTect Reverse Transcription Kit (from QIAGEN). Using the cDNA as a template and Thermal Cycler Dice Real Time System I (Takara Bio Inc.), expression levels of AQP1, SGLT2, Na/K ATPase, Megalin, MDR1, OAT1, OCT2, and, E-cadherin genes were measured by real-time PCR. Megalin and OCT2 genes are markers of renal proximal tubule epithelial cells. Specifically, Megalin is a gene for encoding an acceptor protein involved in re-absorption of proteins. OCT2 (organic cation transporter 2) is a gene for encoding a protein involved in drug transport.

The ratio of the expression level on the Mth (M=4, 10, 16, 56) day of culture relative to the expression level immediately after the formation of the cell monolayer (dM/d0) was calculated for each gene. Results are summarized in FIG. 7. FIG. 7 is a chart summarizing time-dependent changes in gene expression levels in human renal proximal tubule epithelial cells cultured in a state of cell monolayer.

As shown in FIG. 7, it was demonstrated that the expression levels of the genes, excluding E-cadherin, rise abruptly on the 16th day of culture as compared to until the 10th day of culture. The gene E-cadherin also exhibited a high expression level on the 16th day of culture. This demonstrated that cells with improved physiological functions can be obtained more reliably by culturing the cells for 16 days or longer in a state in which the human renal proximal tubule epithelial cells form a confluent monolayer. It was also demonstrated that high expression levels are maintained in most genes even on the 56th day of culture. It was therefore demonstrated that cells with improved physiological functions are obtained even on the 56th day of culture.

[Analysis of Effect of Adding Adhesion Molecules to Cell Suspension: Test 3]

Test 3 was carried out to check the impact of addition of adhesion molecules to the cell suspension on the formation of a cell monolayer. First, human renal proximal tubule epithelial cells (Lonza Inc.) were seeded in a 10-cm petri dish (Corning Inc.) and cultured for six days. The cells were peeled and collected by a 0.1% trypsin solution (Lonza Inc.). REGM (Lonza Inc.) was added to the collected cells to prepare the cell suspension with the cell concentration of $3 \times 10^5$ cells/ml. Laminin 511-E8 (iMatrix-511; Nippi Inc.) was added to this cell suspension to result in a predetermined concentration. The concentration of laminin 511-E8 was controlled to be 0, 0.2, 0.8, 1.7, 2.5, 7.5, 17, 33, 83 µg/ml. Converting the concentration into the amount added per a unit area of the culture surface (L511 amount/cm$^2$), 0.00, 0.04, 0.22, 0.44, 0.66, 1.97, 4.39, 8.76, 21.92 µg/cm$^2$ were added.

The cell suspension with each laminin concentration was seeded in an amount of 500 µl in a Corning (registered trademark) CellBIND (registered trademark) 24 well plate (Corning Inc.). The 24 well plate was used immediately after being unsealed. In other words, the plate in which the coating agent layer is not formed was used. The cells were cultured under conditions of 37° C. and 5% $CO_2$. The medium was exchanged every day.

Figure 9:
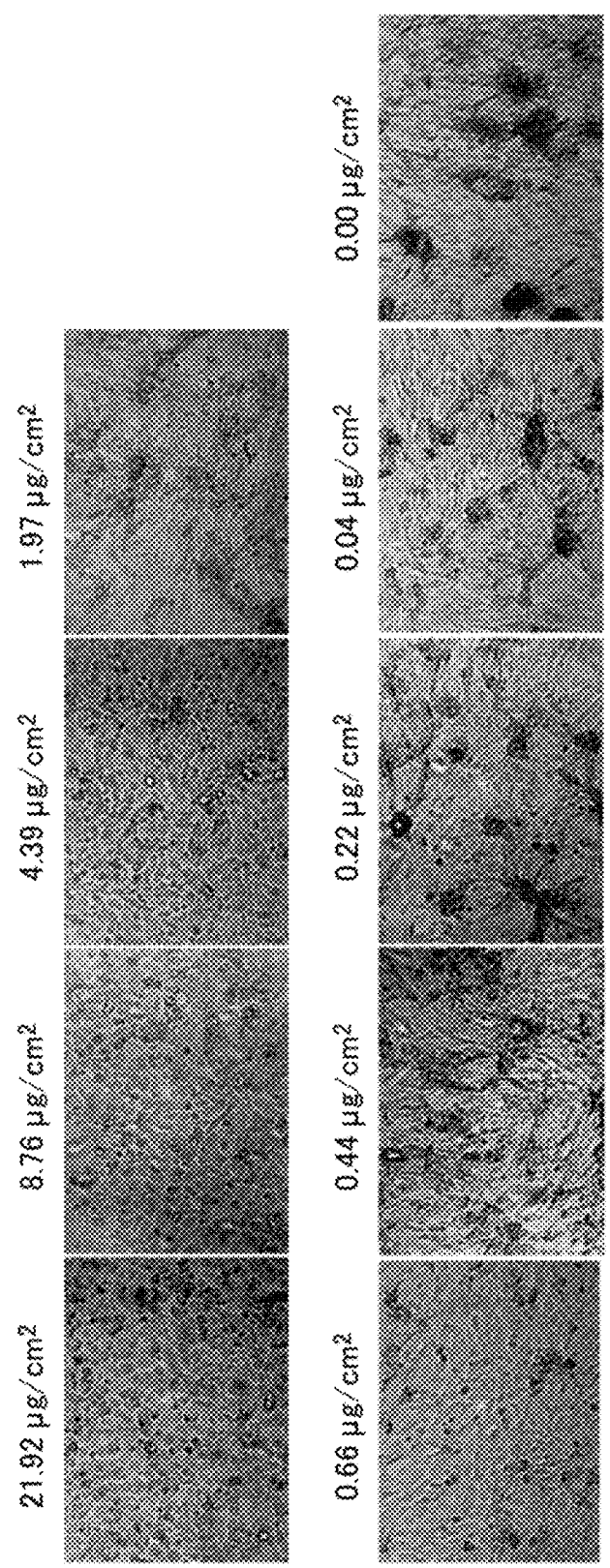
FIG. 9 is an optical micrographic image of cells on the 17th day of culture.

The state of the cells in each plate occurring after 1, 3, 7, 10, 13, 17, 30, 60 days from the seeding was microscopically observed. The case where the cell monolayer is maintained was evaluated as "○". Further, the case where a symptom of aggregation was seen in part but is not so serious as to hinder restoration of physiological functions or usage of the cell support composite, i.e., the case where a substantive monolayer is maintained, was evaluated as "Δ". Further, aggregation to an extent that hinders restoration of physiological functions or usage of the cell support composite were evaluated as "x". In other words, "○" and "Δ" pass the test, and "x" fails the test. Results are summarized in FIG. 8. As a typical example, an optical micrographic image (magnification factor×100) of cells in each plate after 17 days from the seeding is shown in FIG. 9. FIG. 8 shows a relationship between the concentration of the adhesion molecules and the time-dependent change in the state of the cell monolayer. FIG. 9 is an optical micrographic image of cells on the 17th day of culture.

As shown in FIG. 8, an aggregate of cells was observed on the 10th day of culture when laminin 511-E8 as the adhesion molecules was not added to the cell suspension (0 µg/cm$^2$). When laminin 511-E8 was added to the cell suspension in an amount of 0.04 µg/cm$^2$, on the other hand, no aggregates were observed on the 10 day of culture, and an aggregate was observed on the 13th day of culture. It was demonstrated from this that the cell monolayer can be stabilized, and the duration for which the monolayer is maintained can be extended, by adding the adhesion molecules to the cell suspension.

An aggregate was observed on the 13th day of culture when the amount added was 0.22 µg/cm$^2$, but no aggregates were observed on the 13th day of culture when the amount added was 0.44 µg/cm$^2$. It was demonstrated from this that it is more preferred that the concentration of fragmented laminin as the adhesion molecules be in excess of 0.22 µg/cm$^2$. In the case the amount added was 0.66 µg/cm$^2$, an aggregate was observed on the 17th day of culture. In the case the amount added was 1.97 µg/cm$^2$, however, no aggregates were observed on the 17th day of culture (see also FIG. 9). It was demonstrated from this that it is more preferred that the concentration of fragmented laminin as the adhesion molecules be in excess of 0.66 µg/cm$^2$. In the case the amount added was 1.97 µg/cm$^2$, an aggregate was observed on the 60th day of culture. In the case the amount added was 4.39 µg/cm$^2$, however, no aggregates were observed on the 60th day of culture. It was demonstrated from this that it is more preferred that the concentration of fragmented laminin as the adhesion molecules be in excess of 1.97 µg/cm$^2$.

[Analysis of Effect of Combination of Addition of Adhesion Molecules and Coating Agent Layer; Test 4]

Test 4 was carried out to check the impact of a combination of addition of adhesion molecules to the cell suspension and the coating agent layer formed on the substrate on the cell monolayer. First, as in Test 3, the cell suspension with the cell concentration of $3 \times 10^5$ cells/ml was prepared. laminin 511-E8 (iMatrix-511: Nippi Inc.) was added to this cell suspension to result in the same concentration as that of Test 3.

Further, REGM (Lonza Inc.) was added in an amount of 300 µl to the Corning (registered trademark) CellBIND (registered trademark) 24 well plate (Corning Inc.), and the 24 well plate was rested at 4° C. for 24 hours. Subsequently, the plate was rested at 37° C. two hours before cell seeding, and REGM was removed immediately before cell seeding. In this way, the coating agent layer is formed on the culture surface of the 24 well plate. The cell suspension with each laminin concentration was seeded in an amount of 500 µl in the plate in which the coating agent layer is formed. The cells are then cultured under conditions of 37° C. and 5% $CO_2$. The medium was exchanged every day.

Figure 11:
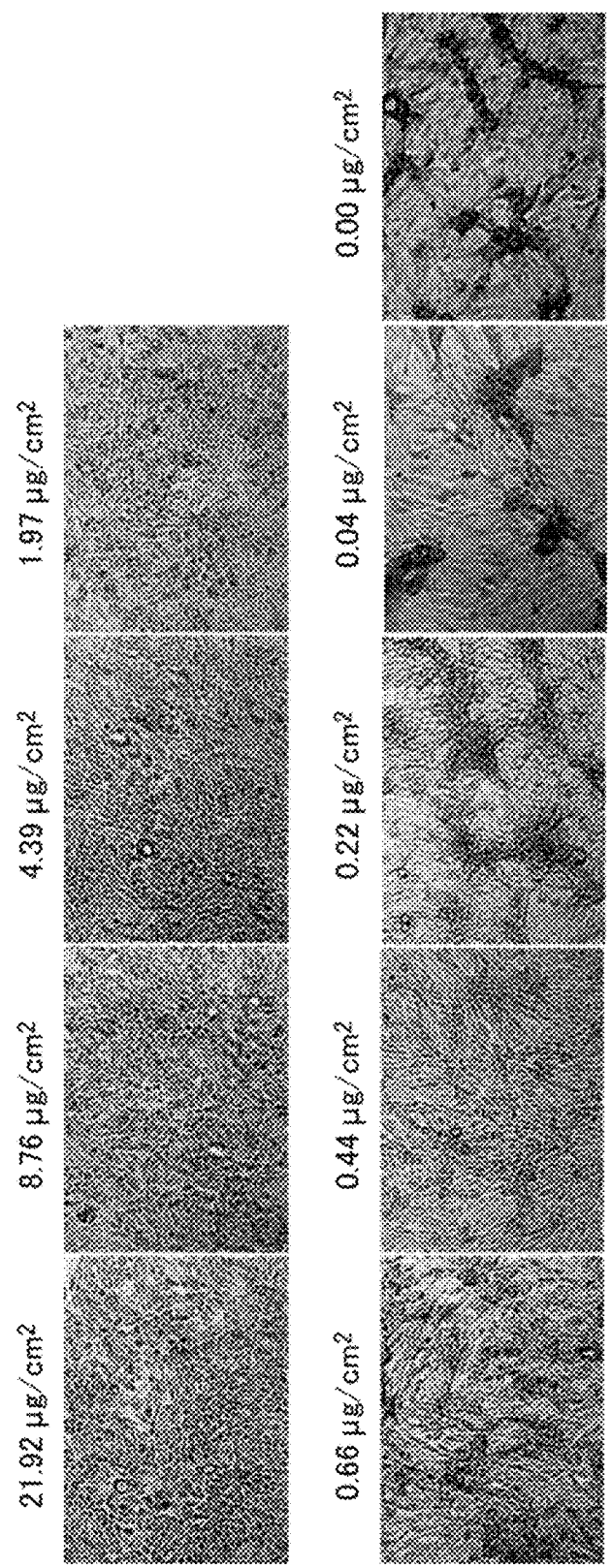
FIG. 11 is an optical micrographic image of cells on the 17th day of culture.

The state of the cells in each plate occurring after 1, 3, 7, 10, 13, 17, 30, 60 days from the seeding was microscopically observed, and the state of the cells was evaluated as in Test 3. Results are summarized in FIG. 10. As a typical example, an optical micrographic image (magnification factor×100) of cells in each plate after 17 days have from the seeding is shown in FIG. 11. FIG. 10 shows a relationship between the concentration of the adhesion molecules and the time-dependent change in the state of the cell monolayer in the case the coating agent layer is formed. FIG. 11 is an optical micrographic image of cells on the 17th day of culture.

An aggregate was observed on the 13th day of culture when laminin was added in an amount of 0.22 μg/cm² in the absence of the coating agent layer (see FIG. 8). In the presence of the coating agent layer, no aggregates were observed on the 13th day as shown in FIG. 10. When the substrate is provided with the coating agent layer, and the amount added was 0.22 μg/cm², an aggregate was observed on the 17th day of culture. Further, an aggregate was observed on the 17th day of culture when the amount added was 0.44 μg/cm² and 0.66 μg/cm² in the absence of the coating agent layer (see FIG. 8). In the presence of the coating agent layer, no aggregates were observed on the 17th day (see also FIG. 11). When the substrate is provided with the coating agent layer, and the amount added was 0.44 μg/cm² and 0.66 μg/cm², no aggregates were observed even on the 60th day of culture.

It was demonstrated from this that the structure of the cell monolayer can be maintained stable for a longer period of time, by forming a coating agent layer on the culture surface of the substrate before placing the cell suspension. Further, on the 17th day of culture, an aggregate was observed when the amount added was 0.66 μg/cm² or smaller in the absence of the coating agent layer. In the presence of the coating agent layer, an aggregate was observed when the amount added was 0.22 μg/cm² or smaller. In other words, it was demonstrated that providing the coating agent layer can reduce the amount of adhesion molecules necessary to maintain the cell monolayer.

Culturing cells in Test 4 by adding an amount 0.00 μg/cm² uses the same condition as Test 2 in that the adhesion molecules are not added to the cell suspension, and the coated plate is used. Meanwhile, an aggregate was observed on the 10th day of culture in Test 4, but the cell monolayer was maintained even after 56 days of culture in Test 2. The difference is estimated to derive from the difference in the amount in which the cell adhesion substance is applied or the difference in the tendency for aggregation between cell lots used in Test 2 and those in Test 4. It can however be understood from Test 4 that addition of the adhesion molecules to the cell suspension can stabilize the cell monolayer.

[Analysis of Type of Adhesion Molecule: Test 5]

Test 5 was carried out to check the type of adhesion molecules useful to maintain the structure of the cell monolayer. In this test, the cell suspension with each laminin concentration was prepared, and the cells were seeded and cultured in the same manner as in Test 3 except that laminin 511 (Biolamina), a full-length laminin, was used in place of laminin 511-E8, and tests at some laminin concentrations were omitted. The laminin concentrations checked in Test 5 are 0, 0.8, 2.5, 7.5, 33 μg/ml (0.00, 0.22, 0.66, 1.97, 8.76 μg/cm²).

Figure 13:
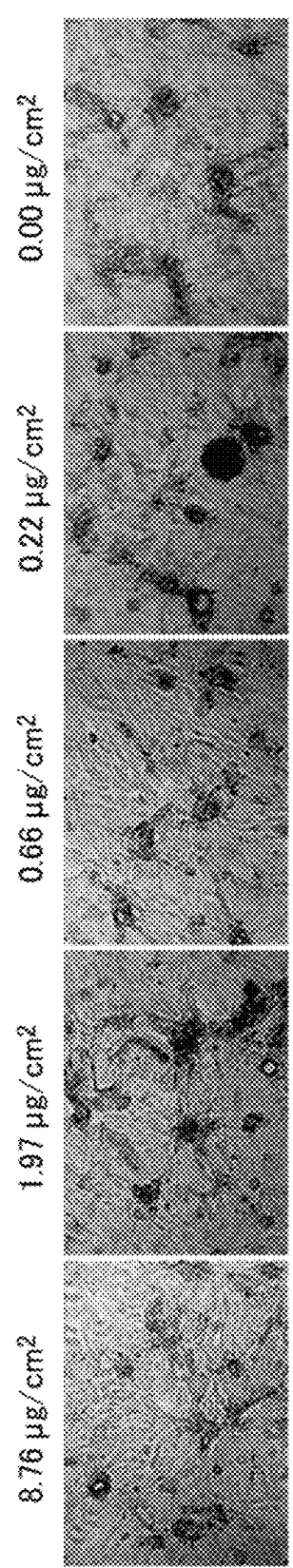
FIG. 13 is an optical micrographic image of cells on the 17th day of culture.

The state of the cells in each plate occurring after 1, 3, 7, 10, 13, 17, 30, 60 days from the seeding was microscopically observed, and the state of the cells was evaluated as in Test 3. Results are summarized in FIG. 12. As a typical example, an optical micrographic image (magnification factor×100) of cells in each plate after 17 days from the seeding is shown in FIG. 13. FIG. 12 shows a relationship between the concentration of the full-length laminin and the time-dependent change in the state of the cell monolayer. FIG. 13 is an optical micrographic image of cells on the 17th day of culture.

As shown in FIGS. 12 and 13, the effect of maintaining the shape of the cell monolayer, which was observed in the case the fragmented laminin was added, was not observed when the full-length laminin was added to the cell suspension. It was demonstrated from this that it is necessary to add fragments of laminin molecules to the cell suspension in order to maintain the shape of the cell monolayer in a stable manner for a long period of time. The inventors have confirmed that the same effect as provided by the fragmented laminin is provided by a fragmented basement membrane matrix mixture and a full-length basement membrane matrix mixture. The effect of the full-length basement membrane matrix mixture will be described in Test 6 below.

[Analysis of Effect of Adding Full-length Basement Membrane Matrix Mixture to Cell Suspension: Test 6]

Test 6 was carried out to check the impact of addition of a full-length basement membrane matrix mixture to the cell suspension on the formation of a cell monolayer. First, human renal proximal tubule epithelial cells (Lonza Inc.) were seeded in a 10-cm petri dish (Corning Inc.) and cultured for six days. The cells were peeled and collected by a 0.1% trypsin solution (Thermo Fisher Scientific Inc.). REGM (Lonza Inc.) was added to the collected cells to prepare the cell suspension with the cell concentration of 3×10⁵ cells/ml. The first Matrigel (Corning Inc.) or the second Matrigel (Corning Inc.) was added as a full-length basement membrane matrix mixture to the cell suspension to result in a predetermined concentration. As described above, the first Matrigel is a normal Matrigel that contains a growth factor, and the second Matrigel is a Matrigel having the growth factor reduced therein as compared with the first Matrigel (Growth Factor Reduced Matrigel Matrix).

The concentration of the first Matrigel in the cell suspension was controlled to be 5.0, 25, 100, 500, 1000, 2500, 5000 μg/ml. Converting the concentration into the amount added per a unit area of the culture surface (the amount of the first Matrigel/cm²), 1.3, 6.6, 26, 132, 263, 658, 1316 μg/cm² were added. The concentration of the second Matrigel in the cell suspension was controlled to be 5.0, 25, 100, 400, 1000, 2500, 4000 μg/ml. Converting the concentration into the amount added per a unit area of the culture surface (the amount of the second Matrigel/cm²), 1.3, 6.6, 26, 105, 263, 658, 1053 μg/cm² were added.

Each cell suspension was seeded in an amount of 500 μl in a Corning (registered trademark) CellBIND (registered trademark) 24 well plate (Corning Inc.). This 24 well plate is a plate in which the coating agent layer is not formed. The cells were cultured under conditions of 37° C. and 5% $CO_2$. The medium was exchanged every two days.

The adhesion state of the cells in each plate occurring after 3, 7, 10, 13, 17, 21 days from the seeding was microscopically observed. The state of the cells was evaluated as in Test 3. Results are summarized in FIG. 14. As a typical example, an optical micrographic image (magnification factor×100) of cells in some plates after 17 days from the seeding is shown in FIG. 15. FIG. 14 shows a relationship between the concentration of the first, second Matrigel and the time-dependent change in the state of the cell monolayer. FIG. 15 is an optical micrographic image of cells on the 17th day of culture.

As shown in FIG. 15, an aggregate of cells was observed on the 17th day of culture when the first Matrigel or the second Matrigel was added to the cell suspension in an amount of 1.3 μg/cm². Further, it was observed that, when the first Matrigel was added to the cell suspension in an amount of 1316 μg/cm² and when the second Matrigel was added to the cell suspension in an amount of 1053 μg/cm², the cells were arranged in a net-like pattern on the 17th day of culture. In other words, it was observed that the cell monolayer is not maintained. Meanwhile, it was observed that, when the first Matrigel was added to the cell suspension in an amount of 132 μg/cm² and when the second Matrigel was added to the cell suspension in an amount of 105 µg/cm², the cells formed a monolayer on the 17th day of culture.

Further, as shown in FIG. 14, an aggregate of cells was observed on the 10th day of culture and after, when the first Matrigel or the second Matrigel was added to the cell suspension in an amount of 1.3 µg/cm². Further, it was observed that, when the first Matrigel was added to the cell suspension in an amount of 1316 µg/cm² and when the second Matrigel was added to the cell suspension in an amount of 1053 µg/cm², the cells were distributed in a net-like pattern on the third day of culture, and this state was maintained until the 21st day of culture. It was demonstrated from this that the concentration of a full-length basement membrane matrix mixture added as the adhesion molecules is preferably more than 1.3 µg/cm² and less than 1053 µg/cm².

It was also observed that the cell monolayer is substantially maintained until the 21st day of culture when the first Matrigel or the second Matrigel was added in an amount not less than 6.6 µg/cm² and not more than 658 µg/cm². It was demonstrated from this that the concentration of a full-length basement membrane matrix mixture added as the adhesion molecules is preferably not less than 6.6 µg/cm² and not more than 658 µg/cm².

It was further demonstrated that the cell monolayer collapses in part until the 21st day of culture when the first Matrigel or the second Matrigel was added in an amount of 6.6 µg/cm² (A evaluation on the 17th day of culture in the case of the first Matrigel, and A evaluation on the 13th day of culture in the case of the second Matrigel). Meanwhile, collapse of the cell monolayer was not observed until the 21st day of culture when the amount added was 26 µg/cm². It was demonstrated from this that the concentration of a full-length basement membrane matrix mixture added as the adhesion molecules is more preferably more than 6.6 µg/cm² and, even more preferably, 26 µg/cm² or more.

It was also observed that, when the second Matrigel was added in an amount of 658 µg/cm², the cell monolayer is turned into a net-like pattern in part on the 13th day of culture. Meanwhile, collapse of the cell monolayer was not observed until the 21st day of culture when the amount added was 263 µg/cm². It was demonstrated from this that the concentration of the second Matrigel as the adhesion molecules is more preferably less than 658 µg/cm² and, even more preferably, 263 µg/cm² or less.

What is claimed is:

1. A method of culturing cells, comprising:
    placing a cell suspension including i) one of more types of adhesion molecules selected from the group consisting of a variant of E8 region containing a cell adhesion site of Domain I in laminin 511 and a complete basement membrane matrix mixture and ii) renal proximal tubule epithelial cells on a culture surface of a substrate; and
    culturing the renal proximal tubule epithelial cells on the substrate to form a confluent monolayer of the cells,
    wherein a concentration of the variant of E8 region containing the cell adhesion site of Domain I in laminin 511 in the cell suspension is not less than 0.44 µs/cm², and
    wherein a concentration of the complete basement membrane matrix mixture in the cell suspension is not less than 6.6 µg/cm² and not more than 658 µg/cm².

2. The method of culturing cells according to claim 1, wherein the concentration of the variant of E8 region containing the cell adhesion site of Domain I in laminin 511 in the cell suspension is not less than 0.66 µg/cm² of the culture surface.

3. The method of culturing cells according to claim 1, wherein the concentration of the complete basement membrane matrix mixture in the cell suspension is not less than 26 µg/cm² and not more than 263 µg/cm² of the culture surface.

4. The method of culturing cells according to claim 1, further comprising:
    coating the culture surface with a cellular adhesive substance,
    wherein the placing includes placing the cell suspension on the culture surface coated with the cellular adhesive substance.

5. A method of manufacturing a cell support composite including a substrate and a confluent monolayer of cultured cells stacked on a culture surface of the substrate, comprising:
    forming the monolayer on the substrate by the method of culturing cells according to claim 1.

6. The method of culturing cells according to claim 1, wherein the concentration of the variant of E8 region containing the cell adhesion site of Domain I in laminin 511 in the cell suspension is not less than 1.97 µg/cm² of the culture surface.

7. The method of culturing cells according to claim 1, wherein the concentration of the variant of E8 region containing the cell adhesion site of Domain I in laminin 511 in the cell suspension is not less than 4.39 µg/cm² of the culture surface.

8. The method of culturing cells according to claim 1, wherein the concentration of the complete basement membrane matrix mixture in the cell suspension is not less than 105 µg/cm² of the culture surface.

* * * * *